United States Patent
Reddy et al.

(10) Patent No.: US 9,434,773 B2
(45) Date of Patent: Sep. 6, 2016

(54) PLANTS HAVING STRESS RELATED TRAITS AND METHODS FOR MAKING THE SAME

(75) Inventors: Avutu S. Reddy, Carmel, IN (US); Sun Yuejin, Westfield, IN (US); Donald J. Merlo, Carmel, IN (US); Weiting W. Ni, Carmel, IN (US); Dayakar Pareddy, Carmel, IN (US); Zhifang Gao, Carmel, IN (US); Gregory A. Bradfisch, Carmel, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 488 days.

(21) Appl. No.: 13/617,207

(22) Filed: Sep. 14, 2012

(65) Prior Publication Data

US 2013/0067617 A1   Mar. 14, 2013

Related U.S. Application Data

(60) Provisional application No. 61/534,547, filed on Sep. 14, 2011.

(51) Int. Cl.
| | | |
|---|---|---|
| *A01H 5/00* | (2006.01) | |
| *A01H 5/10* | (2006.01) | |
| *C12N 15/82* | (2006.01) | |
| *C12N 9/00* | (2006.01) | |
| *C07K 14/415* | (2006.01) | |

(52) U.S. Cl.
CPC .............. *C07K 14/415* (2013.01); *C12N 9/93* (2013.01); *C12N 15/8273* (2013.01); *C12Y 603/02019* (2013.01)

(58) Field of Classification Search
None
See application file for complete search history.

(56) References Cited

U.S. PATENT DOCUMENTS

| | | | |
|---|---|---|---|
| 5,380,831 A | 1/1995 | Adang et al. | |
| 5,510,474 A | 4/1996 | Quail et al. | |
| 5,641,876 A | 6/1997 | McElroy et al. | |
| 5,767,339 A * | 6/1998 | McCurdy | 800/320.1 |
| 6,166,302 A | 12/2000 | Merlo et al. | |
| 6,384,207 B1 | 5/2002 | Ainley et al. | |
| 7,179,902 B2 | 2/2007 | Cowen et al. | |
| 2008/0034449 A1* | 2/2008 | Han et al. | 800/278 |

FOREIGN PATENT DOCUMENTS

WO   WO 97/13402 A1   4/1997

OTHER PUBLICATIONS

Freemont (Current Biology 2000, 10: 84-87).*
Chen et al (Molecular Plant, Advanced Access Published on May 9, 2013).*
Paterson el al (GenBank Accession No. XM_002452547—first available online: Jun. 25, 2009).*
Ryu et al (Plant Physiology, Dec. 2010, vol. 154, pp. 1983-1997).*
Bae et al (Plant Science 180 (2011) 775-782—first published online: Mar. 4, 2011).*
Gao et al (Plant Mol Biol (2011) 76:145-156—first published online: Apr. 16, 2011).*
Sari-Gorla et al (Theor Appl Genet (1999) 99: 280-288).*
Higgins, Methods in Molecular Biology, vol. 25. (1994) Computer Analysis of Sequence Data, Part II.*
Thompson et al (Nucleic Acids Research, 1994, vol. 22, No. 22 4673-4680).*
Ma et al (Gene 444 (2009) 33-45).*
Allen, R. G., L. S. Pereira, D. Raes, and M. Smith. 1998. Crop evapotranspiration: guidelines for computing crop requirements, Food and Agriculture Organization of the United Nations Conference on Irrigation and Drainage vol. Paper No. 56, Rome, Italy.
Bolanos, J., G. O. Edmeades, and L. Martinez. 1993. Eight cycles of selection for drought tolerance in lowland tropical maize. III. Responses in drought-adaptive physiological and morphological traits. Field Crops Research 31:269-286.
Frame, B., M. Main, R. Schick, and K. Wang. 2011. Genetic Transformation Using Maize Immature Zygotic Embryos p. 327-341. In T. A. Thorpe and E. C. Yeung (ed.), Plant Embryo Culture Methods and Protocols: Methods in Molecular Biology. Springer Science and Business Media, LLC.
Oltmanns, H., B. Frame, L.-Y. Lee, S. Johnson, B. Li, K. Wang, and S. B. Gelvin. 2010. Generation of Backbone-Free, Low Transgene Copy Plants by Launching T-DNA from the Agrobacterium Chromosome. Plant Physiology 152:1158-1166.
Paz, M. M., J. C. Martinez, A. B. Kalvig, T. M. Fonger, and K. Wang. 2006. Improved cotyledonary node method using an alternative explant derived from mature seed for efficient Agrobacterium-mediated soybean transformation. Plant Cell Reports 25:206-213.
Selmani, A., and C. E. Wassom. 1993. Daytime chlorophyll fluorescence measurement in field-grown maize and its genetic variability under well-watered and water-stressed conditions. Field Crops Research 31:173-184.
Sinclair, T. R., and M. M. Ludlow. 1986. Influence of soil-water supply on the plant water-balance of four tropical grain legumes. Australian Journal of Plant Physiology 13:329-341.
Zeng, P., D. Vadnais, Z. Zhang, and J. Polacco. 2004. Refined glufosinate selection in Agrobacterium-mediated transformation of soybean [*Glycine max* (L.) Merr.]. Plant Cell Reports 22:478-482.

* cited by examiner

*Primary Examiner* — Lee A Visone
(74) *Attorney, Agent, or Firm* — Marcos P. Rivas

(57) ABSTRACT

This invention relates generally to a plant cell with increased yield, preferably under condition of transient and repetitive abiotic stress as compared to a corresponding non-transformed wild type plant cell by increasing or generating one or more activities of RING proteins in plants.

22 Claims, 1 Drawing Sheet

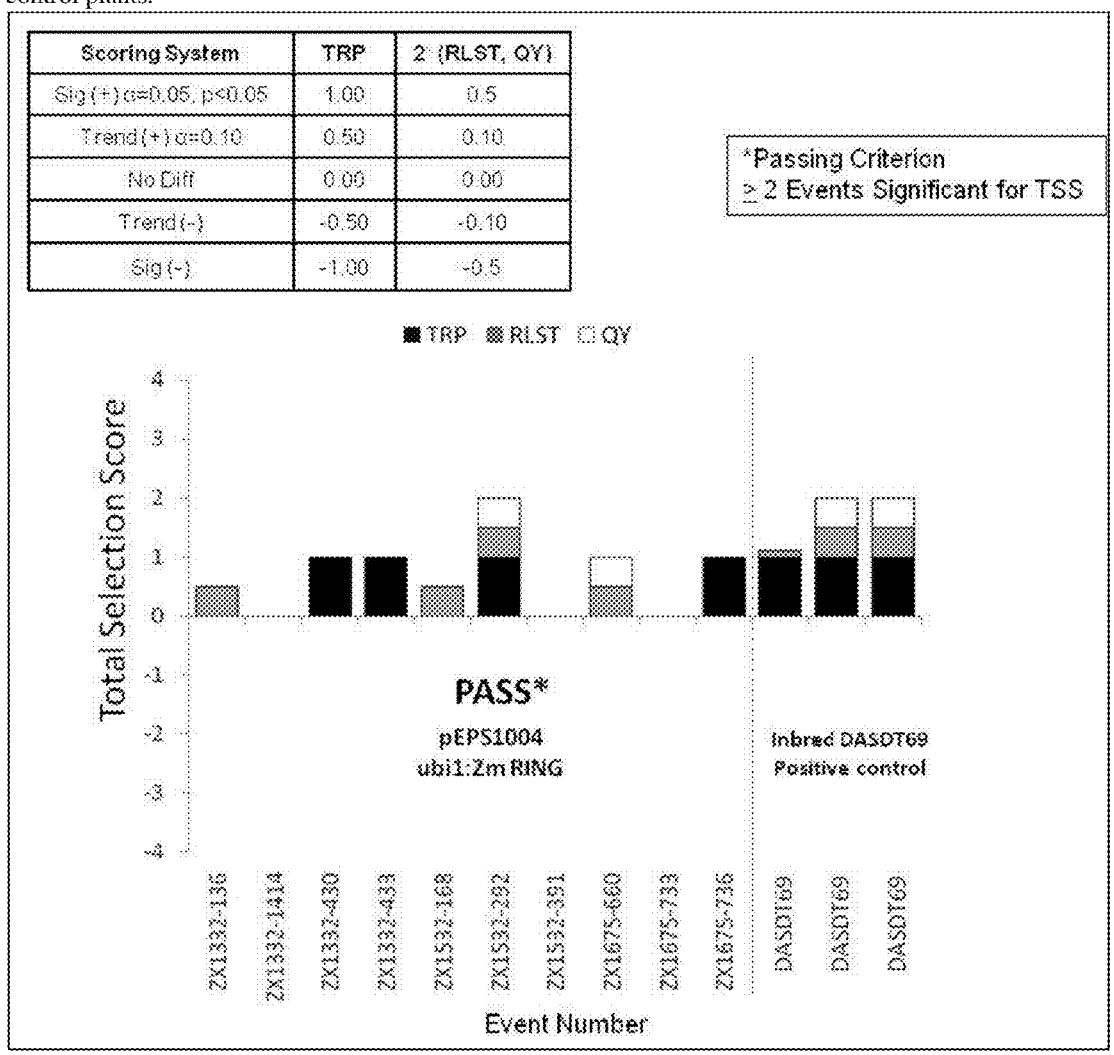
Total Selection Scores for ZmRING maize events compared to nontransgenic drought tolerant control plants.

PLANTS HAVING STRESS RELATED TRAITS AND METHODS FOR MAKING THE SAME

CROSS REFERENCE TO RELATED APPLICATIONS

The present application claims priority to U.S. Provisional Application No. 61/534,547 filed on Sep. 14, 2011, the entire contents of which are incorporated herein by reference.

TECHNICAL FIELD

The present invention disclosed herein provides a method for producing a plant having improved stress tolerance with drought tolerance as compared to a corresponding wild type plant, such method comprising increasing or generating one or more activities in a plant or a part thereof. The present invention further relates to nucleic acids encoding for and enhancing or improving one or more traits of a transgenic plant, and cells, progenies, seeds and pollen derived from such plants or parts, as well as methods of making and methods of using such plant cell(s) or plant(s), progenies, seed(s) or pollen. Particularly, improved trait(s) can manifested in an increased yield, preferably by improving one or more yield-related trait(s) as a result of drought tolerance. This invention relates generally to a plant cell with increased yield, preferably under condition of transient and repetitive abiotic stress as compared to a corresponding non-transformed wild type plant cell by increasing or generating one or more activities of a RING protein in plants. In particular, this invention relates to plants tailored to grow under conditions of transient and/or repetitive abiotic stress and/or of nutrient deficiency. The invention also deals with methods of producing and screening for and breeding such plant cells or plants.

BACKGROUND

Population increases and climate change have brought the possibility of global food, feed, and fuel shortages into sharp focus in recent years. Under field conditions, plant performance, for example in terms of growth, development, biomass accumulation and seed generation, depends on a plant's tolerance and acclimation ability to numerous environmental conditions, changes and stresses. Since the beginning of agriculture and horticulture, there was a need for improving plant traits in crop cultivation. Breeding strategies foster crop properties to withstand biotic and abiotic stresses, to improve nutrient use efficiency and to alter other intrinsic crop specific yield parameters, i.e. increasing yield by applying technical advances to cope with such stresses. Plants are sessile organisms and consequently need to cope with various environmental stresses. Biotic stresses such as plant pests and pathogens on the one hand, and abiotic environmental stresses on the other hand are major limiting factors for plant growth and productivity, thereby limiting plant cultivation and geographical distribution. Plants exposed to different stresses typically have low yields of plant material, like seeds, fruit or other produces. Crop losses and crop yield losses caused by abiotic and biotic stresses represent a significant economic and political factor and contribute to food shortages, particularly in many underdeveloped countries.

Plants are exposed during their life cycle also to various cold, drought, salt, cold germination, heat, and other abiotic stresses, and viral, fungal, bacterial and other biotic stresses. For example drought stress is often manifested primarily as osmotic stress, leading to the disruption of homeostasis and ion distribution in the cell (Serrano et al., 1999; Zhu, 2001a; Wang et al., 2003). Oxidative stress, which frequently accompanies high temperature, salinity or drought stress, may cause denaturation of functional or structural proteins (Smirnoff, 1998). As a consequence these, abiotic stresses often activate similar signaling pathways (Shinozaki and Ymaguchi-Shinozaki, 2000; Knight and Knight, 2001; Zhu 2001b, 2002) and cellular responses, e.g. the production of certain stress proteins, anti-oxidants and compatible solutes (Vierling and Kimpel, 1992; Zhu et al., 1997; Cushman and Bohnert, 2000). Under freezing temperatures, plant cells can lose water as a result of ice formation that starts in the apoplast and withdraws water from the symplast (McKersie and Leshem, 1994. Stress and Stress Coping in Cultivated Plants, Kluwer Academic Publishers). Physiologically these stresses are also interconnected and may induce similar cellular damage. Additionally, plants may be under salt stress. The protection strategies are similar to those of drought resistance. Since high salt content in some soils results in less available water for cell intake, its effect is similar to those observed under drought conditions.

Drought, heat, cold and salt stress have a common theme important for plant growth and that is water availability. Plants are typically exposed during their life cycle to conditions of reduced environmental water availability. Most plants have evolved strategies to protect themselves against these conditions of low water or desiccation. However, if the severity and duration of the drought are too great, the effects on plant development, growth and yield of most crop plants are profound. Such conditions are to be expected in the future due to climatic change. According to one accepted scenario of climate change, not only the weather is more variable, but the average temperature is hotter and the average rainfall is less than in the past. Most plants are not able to keep up the adaption of their protection strategies to the climatic change. Continuous exposure to drought causes major alterations in the plant metabolism. These great changes in metabolism ultimately lead to cell death and consequently yield losses.

Therefore, there is the need for inventions that are useful to farmers to limit their losses due to biotic and abiotic stress

BRIEF SUMMARY OF THE INVENTION

Embodiments of the present invention include plants comprising recombinant DNA constructs comprising at least one polynucleotide operably linked to at least one regulatory element, wherein said polynucleotide has a nucleic acid sequence of at least 80%, 85%, 90%, 95%, 96%, 97%, 98%, 99% or 100% sequence identity, when compared to SEQ ID NOs: 1 or 3. Such plants can exhibit increased drought tolerance or an increase in yield when compared to a control plant not comprising said recombinant DNA construct. Such plant is a moncot and more preferably corn.

Embodiments of the present invention include methods of increasing drought and/or heat tolerance in a plant by introducing into a regenerable plant cell a recombinant DNA construct comprising a polynucleotide operably linked to at least one regulatory sequence, wherein the polynucleotide has a nucleic acid sequence of at least 80%, 85%, 90%, 95%, 96%, 97%, 98%, 99% or 100% sequence identity, when compared to SEQ ID NOs: 1 or 3; and then regenerating a transgenic plant from the regenerable plant cell after the first step, wherein the transgenic plant comprises in its genome the recombinant DNA construct and exhibits increased drought tolerance when compared to a control plant not comprising the recombinant DNA construct.

Embodiments can further include obtaining a progeny plant derived from the transgenic plants, wherein said progeny plant comprises in its genome the recombinant DNA construct and exhibits increased drought tolerance when compared to a control plant not comprising the recombinant DNA construct.

Additional embodiments can include methods of evaluating drought and/or heat tolerance in a plant by introducing into a regenerable plant cell a recombinant DNA construct comprising a polynucleotide operably linked to at least one regulatory sequence, wherein the polynucleotide has a nucleic acid sequence of at least 80%, 85%, 90%, 95%, 96%, 97%, 98%, 99% or 100% sequence identity, when compared to SEQ ID NOs: 1 or 3; regenerating a transgenic plant from the regenerable plant cell after the first step, wherein the transgenic plant comprises in its genome the recombinant DNA construct; and then evaluating the transgenic plant for drought tolerance compared to a control plant not comprising the recombinant DNA construct.

Embodiments can further include obtaining a progeny plant derived from the transgenic plant, wherein the progeny plant comprises in its genome the recombinant DNA construct; and then evaluating the progeny plant for drought tolerance compared to a control plant not comprising the recombinant DNA construct.

Other embodiments include methods of determining an alteration of an agronomic characteristic in a plant, comprising introducing into a regenerable plant cell a recombinant DNA construct comprising a polynucleotide operably linked to at least one regulatory sequence, wherein the polynucleotide has a nucleic acid sequence of at least 80%, 85%, 90%, 95%, 96%, 97%, 98%, 99% or 100% sequence identity, SEQ ID NOs: 1 or 3; regenerating a transgenic plant from the regenerable plant cell after the first step, wherein the transgenic plant comprises in its genome the recombinant DNA construct; and (determining whether the transgenic plant exhibits an alteration of at least one agronomic characteristic when compared to a control plant not comprising the recombinant DNA construct. Such methods can also include wherein the determining step comprises determining whether the transgenic plant exhibits an alteration of at least one agronomic characteristic when compared, under water limiting conditions, to a control plant not comprising the recombinant DNA construct.

Other embodiments include an isolated nucleic acid comprising a nucleotide sequence encoding SEQ ID NO: 2, wherein SEQ ID NO: 2 increases the maintenance of membrane integrity under abiotic stress in a plant cell. Such abiotic stress is selected from the group consisting of cold, drought, salt, cold germination, and heat. Such nucleotide sequence can be operably linked to at least one regulatory element.

Embodiments also include wherein the nucleic acid is SEQ ID No 1 or 3, complements thereof wherein said nucleic acid molecule hybridizes to one another with sufficient stability to remain annealed to one another under at least low stringency conditions of washing with a salt solution having a concentration of about 2.0x sodium chloride/sodium citrate (SSC) at 50° C. and a nucleic acid that has at least 90% sequence identity to the RING protein.

Methods can also include improving stress tolerance and/or yield stability in a plant cell, the method comprising introducing into the plant cell a nucleic acid comprising a nucleotide sequence encoding a SEQ ID NO: 2, wherein SEQ ID NO: 2 improves stress tolerance and/or yield stability in the plant cell.

Additional embodiments include methods for making a plant having an drought related trait relative to a control plant by introducing a construct of interest into a plant cell, plant, or part thereof, wherein the increased yield-related trait are is one or more of: (i) increased early vigor; (ii) increased biomass; (iii) increased total seed yield per plant; (iv) increased seed filling rate; (v) increased harvest index; (vi) increased thousand kernel weight, (vii) increased abiotic stress resistance, and/or (viii) increased nutrient uptake efficiency.

BRIEF DESCRIPTION OF THE DRAWINGS

In the drawings, which illustrate what is currently considered to be the best mode for carrying out the invention:

FIG. 1 represents selection scores for ZmRING maize transgenic events compared to non-transgenic drought tolerant control plants.

DETAILED DESCRIPTION OF THE INVENTION

The present invention relates to the production of plants having improved stress tolerance that can result in an increased yield as compared to a corresponding wild type plant, comprising increasing or generating one or more activities in a plant or a part thereof, particularly with respect to drought stress. The present invention further relates to nucleic acids encoding for and enhancing or improving one or more traits of a transgenic plant, and cells, progenies, seeds and pollen derived from such plants or parts, as well as methods of making and methods of using such plant cell(s) or plant(s), progenies, seed(s) or pollen. Particularly, said improved trait(s) are manifested in an increased yield, preferably by improving one or more yield-related trait(s) due to drought stress.

Unless otherwise indicated, all technical and scientific terms used herein have the same meaning as they would to one skilled in the art of the present invention. Practitioners are particularly directed to Sambrook et al. Molecular Cloning: A Laboratory Manual (Second Edition), Cold Spring Harbor Press, Plainview, N.Y., 1989, and Ausubel F M et al. Current Protocols in Molecular Biology, John Wiley & Sons, New York, N.Y., 1993, for definitions and terms of the art. It is to be understood that this invention is not limited to the particular methodology, protocols, and reagents described, as these may vary.

As used herein a "plant cell" means a plant cell that is transformed with stably-integrated, non-natural, recombinant DNA, e.g. by *Agrobacterium*-mediated transformation or by bombardment using microparticles coated with recombinant DNA or other means. A plant cell of this invention can be an originally-transformed plant cell that exists as a microorganism or as a progeny plant cell that is regenerated into differentiated tissue, e.g. into a transgenic plant with stably-integrated, non-natural recombinant DNA, or seed or pollen derived from a progeny transgenic plant.

As used herein a "transgenic plant" means a plant whose genome has been altered by the stable integration of recombinant DNA. A transgenic plant includes a plant regenerated from an originally-transformed plant cell and progeny transgenic plants from later generations or crosses of a transformed plant.

As used herein "recombinant DNA" means DNA which has been genetically engineered and constructed outside of a cell including DNA containing naturally occurring DNA or cDNA or synthetic DNA.

As used herein "consensus sequence" means an artificial sequence of amino acids in a conserved region of an alignment of amino acid sequences of homologous proteins, e.g. as determined by a CLUSTALW alignment of amino acid sequence of homolog proteins.

As used herein a "homolog" means a nucleic acid or a protein in a group of proteins that perform the same biological function, e.g. proteins that belong to the same protein family or similar nucleic acids that provide a common enhanced trait in transgenic plants of this invention. Homologs are expressed by homologous genes. With reference to homologous genes, homologs include orthologs, i.e. genes expressed in different species that evolved from common ancestral genes by speciation and encode proteins that retain the same function, but do not include paralogs, i.e. genes that are related by duplication but have evolved to encode proteins with different functions. Homologous genes include naturally occurring alleles and artificially-created variants. Degeneracy of the genetic code provides the possibility to substitute at least one base of the protein encoding sequence of a gene with a different base without causing the amino acid sequence of the polypeptide produced from the gene to be changed. When optimally aligned, homolog genes have at least 50%, 60%, 70%, 80%, 85%, 90%, 95%, 96%, 97%, 98% or 99% or more sequence identity over the full length of the gene identified as being associated with imparting an enhanced trait when expressed in plant cells. In one aspect of the invention homolog genes have a nucleic acid or amino acid sequence similarity that has at least 85%, 90%, 95%, 96%, 97%, 98% or 99% identity to a consensus sequence of proteins, nucleotides and homologs disclosed herein.

Homologs are identified by comparison of amino acid sequence, e.g. manually or by use of a computer-based tool using known homology-based search algorithms such as those commonly known and referred to as BLAST, FASTA, and Smith-Waterman. A local sequence alignment program, e.g. BLAST, can be used to search a database of sequences to find similar sequences, and the summary Expectation value (E-value) used to measure the sequence base similarity. Because a protein hit with the best E-value for a particular organism may not necessarily be an ortholog, i.e. have the same function, or be the only ortholog, a reciprocal query is used to filter hit sequences with significant E-values for ortholog identification. The reciprocal query entails search of the significant hits against a database of amino acid sequences from the base organism that are similar to the sequence of the query protein. A hit can be identified as an ortholog, when the reciprocal query's best bit is the query protein itself or a protein encoded by a duplicated gene after speciation. A further aspect of the homologs encoded by DNA useful in the transgenic plants of the invention are those proteins that differ from a disclosed protein as the result of deletion or insertion of one or more amino acids in a native sequence.

"Percent identity" describes the extent to which the sequences of DNA or protein segments are invariant throughout a window of alignment of sequences, for example nucleotide sequences or amino acid sequences. An "identity fraction" for a sequence aligned with a reference sequence is the number of identical components which are shared by the sequences, divided by the length of the alignment not including gaps introduced by the alignment algorithm. "Percent identity" ("% identity") is the identity fraction times 100. Percent identity is calculated over the aligned length preferably using a local alignment algorithm, such as BLASTp. As used herein, sequences are "aligned" when the alignment produced by BLASTp has a minimal e-value.

"Functional activity" (or "active") is meant herein that the proteins/enzymes for use according to the subject invention have the ability to provide for stress tolerance which can result in an increased yield. Transfer of the functional activity to plant or bacterial systems can involve a nucleic acid sequence, encoding the amino acid sequence for a protein of the subject invention, integrated into a protein expression vector appropriate to the host in which the vector will reside. One way to obtain a nucleic acid sequence encoding a protein with functional activity is to isolate the native genetic material from the bacterial species which produces the protein of interest, using information deduced from the protein's amino acid sequence, as disclosed herein. The native sequences can be optimized for expression in plants, for example, as discussed in more detail below. Optimized polynucleotides can also be designed based on the protein sequence.

The polynucleotides and vectors described herein can be used to transform a number of monocotyledonous (monocot) plants and plant cell systems, including species from one of the following families: *Zea* sp., *Zea may*; *Triticae* sp., *Triticae triticum*, *Hordeum* sp., *Hordeum vulgare*, *Otyza* sp., *Oryza sativa*, sorghum sp., ryegrasses [i.e. *Lolium* species e.g. *Lolium perenne* (perennial ryegrass), *L. multiflorum* (Italian ryegrass) and *L.×boucheanum* (hybrid ryegrass); fescues [i.e. *Festuca* species e.g. *Festuca arundinacea* (tall fescue; syn. *L. arundinaceum*) and *F. pratensis* (meadow fescue; syn. *L. pratense*); *phalaris* [i.e. *Phalaris* species e.g. *Phalaris aquatica* and *Ph. arundinacea*]; dallisgrasses [i.e. *Paspalum* species e.g. *Paspalum dilatatum* and *P. notatum*]; cocksfoot [i.e. *Dactylis glomerata*]; signalgrasses [i.e. *Brachiaria/Urochloa* species e.g. *Brachiaria brizantha*, *B. decumbens*, *B. humidicola* and *Brachiaria* hybrids]; bromegrasses [i.e. *Bromus* species e.g. *Bromus wildenowii* (prarie grass), *B. catharticus* (rescue grass syn *B. unioloides*), and *B. inermis*]; alfalfa [i.e. *medicago sativa*]; clovers [i.e. *Trifolium* species e.g. *Trifolium repens* (white clover), *T. pratense* (red clover)]. Thus, the methods and compositions can be used over a broad range of monocot plant species.

The subject invention encodes for classes of proteins having novel activities as identified herein. One way to characterize these classes of proteins and the polynucleotides that encode them is by defining a polynucleotide by its ability to hybridize, under a range of specified conditions, with an exemplified nucleotide sequence (the complement thereof and/or a probe or probes derived from either strand) and/or by their ability to be amplified by PCR using primers derived from the exemplified sequences.

There are a number of methods for obtaining proteins for use according to the subject invention. For example, antibodies to the proteins disclosed herein can be used to identify and isolate other proteins from a mixture of proteins. Specifically, antibodies may be raised to the portions of the proteins that are most conserved or most distinct, as compared to other related proteins. These antibodies can then be used to specifically identify equivalent proteins with the characteristic activity by immunoprecipitation, enzyme linked immunosorbent assay (ELISA), or immuno-blotting. Antibodies to the proteins disclosed herein, or to equivalent proteins, or to fragments of these proteins, can be readily prepared using standard procedures. Such antibodies are an aspect of the subject invention. Antibodies of the subject invention include monoclonal and polyclonal antibodies, preferably produced in response to an exemplified or suggested protein.

The term "gene fusion construct" as used herein refers to a recombinant nucleic acid sequence comprising cojoined sequences derived from at least two different parental nucleic acids or a chimeric DNA. A "modified gene fusion construct" comprises a subset of gene fusion constructs, in which at least one nucleotide (optionally, in a coding region or linker region) in the construct is modified, or changed, as compared to a parent or wild-type sequence from which that portion of the construct was derived.

As used herein "promoter" means regulatory DNA for initializing transcription. A "plant promoter" is a promoter capable of initiating transcription in plant cells whether or not its origin is a plant cell, e.g. is it well known that *Agrobacterium* T-DNA promoters are functional in plant cells. Thus, plant promoters include promoter DNA obtained from plants, plant viruses and bacteria such as *Agrobacterium* and *Bradyrhizobium* bacteria. Examples of promoters under developmental control include promoters that preferentially initiate transcription in certain tissues, such as leaves, roots, or seeds. Such promoters are referred to as "tissue preferred". Promoters that initiate transcription only in certain tissues are referred to as "tissue specific". A "cell type" specific promoter primarily drives expression in certain cell types in one or more organs, for example, vascular cells in roots or leaves. An "inducible" or "repressible" promoter is a promoter which is under environmental or chemical control. Examples of environmental conditions that may effect transcription by inducible promoters include anaerobic conditions, or certain chemicals, or the presence of light. Tissue specific, tissue preferred, cell type specific, and inducible promoters constitute the class of "non-constitutive" promoters. A "constitutive" promoter is a promoter which is active under most conditions and in most tissues.

As used herein "operably linked" means the association of two or more DNA fragments in a recombinant DNA construct so that the function of one, e.g. protein-encoding DNA, is controlled by the other, e.g. a promoter.

As used herein "expressed" means produced, e.g. a protein is expressed in a plant cell when its cognate DNA is transcribed to mRNA that is translated to the protein.

As used herein "suppressed" means decreased, e.g. a protein is suppressed in a plant cell when there is a decrease in the amount and/or activity of the protein in the plant cell. The presence or activity of the protein can be decreased by any amount up to and including a total loss of protein expression and/or activity.

As used herein a "control plant" means a plant that does not contain the recombinant DNA that imparts an enhanced trait. A control plant is used to identify and select a transgenic plant that has an enhanced trait. A suitable control plant can be a non-transgenic plant of the parental line used to generate a transgenic plant, i.e. devoid of recombinant DNA. A suitable control plant may in some cases be a progeny of a hemizygous transgenic plant line that does not contain the recombinant DNA, known as a negative segregant.

As used herein an "enhanced trait" means a characteristic of a transgenic plant that includes, but is not limited to, an enhanced agronomic trait characterized by enhanced plant morphology, physiology, growth and development, yield, nutritional enhancement, disease or pest resistance, or environmental or chemical tolerance. In more specific aspects of this invention enhanced trait is selected from a group of enhanced traits consisting of enhanced water use efficiency, enhanced cold tolerance, increased yield, enhanced nitrogen use efficiency, enhanced seed protein and enhanced seed oil. In an important aspect of the invention the enhanced trait is enhanced yield including increased yield under non-stress conditions and increased yield under environmental stress conditions. Stress conditions may include, for example, drought, shade, fungal disease, viral disease, bacterial disease, insect infestation, nematode infestation, cold temperature exposure, heat exposure, osmotic stress, reduced nitrogen nutrient availability, reduced phosphorus nutrient availability and high plant density. "Yield" can be affected by many properties including without limitation, plant height, pod number, pod position on the plant, number of internodes, incidence of pod shatter, grain size, efficiency of nodulation and nitrogen fixation, efficiency of nutrient assimilation, resistance to biotic and abiotic stress, carbon assimilation, plant architecture, resistance to lodging, percent seed germination, seedling vigor, and juvenile traits. Yield can also be affected by efficiency of germination (including germination in stressed conditions), growth rate (including growth rate in stressed conditions), ear number, seed number per ear, seed size, composition of seed (starch, oil, protein) and characteristics of seed fill.

Increased yield of a transgenic plant of the present invention can be measured in a number of ways, including test weight, seed number per plant, seed weight, seed number per unit area (i.e. seeds, or weight of seeds, per acre), bushels per acre, tons per acre, or kilo per hectare. For example, corn yield may be measured as production of shelled corn kernels per unit of production area, for example in bushels per acre or metric tons per hectare, often reported on a moisture adjusted basis. Increased yield may result from improved utilization of key biochemical compounds, such as nitrogen, phosphorous and carbohydrate, or from improved responses to environmental stresses, such as cold, heat, drought, salt, and attack by pests or pathogens. Recombinant DNA used in this invention can also be used to provide plants having improved growth and development, and ultimately increased yield, as the result of modified expression of plant growth regulators or modification of cell cycle or photosynthesis pathways. Also of interest is the generation of transgenic plants that demonstrate enhanced yield with respect to a seed component that may or may not correspond to an increase in overall plant yield. Such properties include enhancements in seed oil, seed molecules such as protein and starch, oil components as may be manifested by an alteration in the ratios of seed components.

Recombinant DNA constructs are assembled using methods well known to persons of ordinary skill in the art and typically comprise a promoter operably linked to DNA, the expression of which provides the enhanced agronomic trait. Other construct components may include additional regulatory elements, such as 5' leaders and introns for enhancing transcription, 3' untranslated regions (such as polyadenylation signals and sites), and DNA for transit or signal peptides.

Numerous promoters that are active in plant cells have been described in the literature. These include promoters present in plant genomes as well as promoters from other sources, including nopaline synthase (NOS) promoter and octopine synthase (OCS) promoters carried on tumor-inducing plasmids of *Agrobacterium tumefaciens* and the CaMV35S promoters from the cauliflower mosaic virus as disclosed in U.S. Pat. Nos. 5,164,316 and 5,322,938. Useful promoters derived from plant genes are found in U.S. Pat. No. 5,641,876 which discloses a rice actin promoter, U.S.

Pat. No. 7,151,204 which discloses a maize chloroplast aldolase promoter and a maize aldolase (FDA) promoter, and US Patent Application Publication 2003/0131377 A1 which discloses a maize nicotianamine synthase promoter. These and numerous other promoters that function in plant cells are known to those skilled in the art and available for use in recombinant polynucleotides of the present invention to provide for expression of desired genes in transgenic plant cells.

Furthermore, the promoters may be altered to contain multiple "enhancer sequences" to assist in elevating gene expression. Such enhancers are known in the art. By including an enhancer sequence with such constructs, the expression of the selected protein may be enhanced. These enhancers often are found 5' to the start of transcription in a promoter that functions in eukaryotic cells, but can often be inserted upstream (5') or downstream (3') to the coding sequence. In some instances, these 5' enhancing elements are introns. Particularly useful as enhancers are the 5' introns of the rice actin 1 (see U.S. Pat. No. 5,641,876) and rice actin 2 genes, the maize alcohol dehydrogenase gene intron(s), the maize heat shock protein 70 gene intron (U.S. Pat. No. 5,593,874) and the maize shrunken 1 gene intron. See also US Patent Application Publication 2002/0192813A1 which discloses 5', 3' and intron elements useful in the design of effective plant expression vectors.

It should be appreciated that a heat and/or drought-tolerance polypeptide can include additional amino acids that are not involved in heat and/or drought-tolerance, and thus such a polypeptide can be longer than would otherwise be the case. For example, a heat and/or drought-tolerance polypeptide can include a purification tag, a chloroplast transit peptide, a mitochondrial transit peptide, an amyloplast peptide, or a leader sequence added to the amino or carboxy terminus. In some embodiments, a heat and/or drought-tolerance polypeptide includes an amino acid sequence that functions as a reporter, e.g., a green fluorescent protein or yellow fluorescent protein.

In other aspects of the invention, sufficient expression in plant seed tissues is desired to affect improvements in seed composition. Exemplary promoters for use for seed composition modification include promoters from seed genes such as napin as disclosed in U.S. Pat. No. 5,420,034, maize L3 oleosin as disclosed in U.S. Pat. No. 6,433,252), zein Z27 as disclosed by Russell et al. (1997) Transgenic Res. 6(2): 157-166), globulin 1 as disclosed by Belanger et al (1991) Genetics 129:863-872), glutelin 1 as disclosed by Russell (1997, supra), and peroxiredoxin antioxidant (Perl) as disclosed by Stacy et al. (1996) Plant Mol. Biol. 31(6):1205-1216.

Recombinant DNA constructs useful in this invention will also generally include a 3' element that typically contains a polyadenylation signal and site. Well-known 3' elements include those from *Agrobacterium tumefaciens* genes such as nos 3', tml 3', tmr 3', tms 3', ocs 3', tr73', for example disclosed in U.S. Pat. No. 6,090,627; 3' elements from plant genes such as wheat (*Triticum aesevitum*) heat shock protein 17 (Hspl 73), a wheat ubiquitin gene, a wheat fructose-1,6-biphosphatase gene, a rice glutelin gene, a rice lactate dehydrogenase gene and a rice beta-tubulin gene, all of which are disclosed in US Patent Application Publication 2002/0192813 A1; and the pea (*Pisum sativum*) ribulose biphosphate carboxylase gene (rbs 3'), and 3' elements from the genes within the host plant.

Constructs and vectors may also include a transit peptide for targeting of a gene to a plant organelle, particularly to a chloroplast, leucoplast or other plastid organelle. For descriptions of the use of chloroplast transit peptides see U.S. Pat. No. 5,188,642 and U.S. Pat. No. 5,728,925. For description of the transit peptide region of an *Arabidopsis* EPSPS gene useful in the present invention, see Klee, H J. et al (MGG (1987) 210:437-442).

Recombinant DNA constructs for gene suppression can be designed for any of a number the well-known methods for suppressing transcription of a gene, the accumulation of the mRNA corresponding to that gene or preventing translation of the transcript into protein. Posttranscriptional gene suppression can be practically effected by transcription of RNA that forms double-stranded RNA (dsRNA) having homology to mRNA produced from a gene targeted for suppression.

Gene suppression can also be achieved by insertion mutations created by transposable elements that prevent gene function. For example, transformation with the T-DNA of *Agrobacterium* may be readily achieved and large numbers of transformants can be rapidly obtained. Also, some species have lines with active transposable elements that can efficiently be used for the generation of large numbers of insertion mutations, while some other species lack such options. Mutant plants produced by *Agrobacterium* or transposon mutagenesis and having altered expression of a polypeptide of interest can be identified using the polynucleotides of the present invention. For example, a large population of mutated plants may be screened with polynucleotides encoding the polypeptide of interest to detect mutated plants having an insertion in the gene encoding the polypeptide of interest.

Transgenic plants may comprise a stack of one or more polynucleotides disclosed herein resulting in the production or suppression of multiple polypeptide sequences. Transgenic plants comprising stacks of polynucleotide sequences can be obtained by either or both of traditional breeding methods or through genetic engineering methods. These methods include, but are not limited to, breeding individual lines each comprising a polynucleotide of interest, transforming a transgenic plant comprising a gene disclosed herein with a subsequent gene, and co-transformation of genes into a single plant cell. Co-transformation of genes can be carried out using single transformation vectors comprising multiple genes or genes carried separately on multiple vectors.

Transgenic plants comprising or derived from plant cells of this invention transformed with recombinant DNA can be further enhanced with stacked traits, e.g. a crop plant having an enhanced trait resulting from expression of DNA disclosed herein in combination with herbicide and/or pest resistance traits. For example, genes of the current invention can be stacked with other traits of agronomic interest, such as a trait providing herbicide resistance, or insect resistance, such as using a gene from *Bacillus thuringiensis* to provide resistance against lepidopteran, coleopteran, homopteran, hemipteran, and other insects. Herbicides for which transgenic plant tolerance has been demonstrated and the method of the present invention can be applied include, but are not limited to, glyphosate, dicamba, glufosinate, sulfonylurea, bromoxynil and norflurazon herbicides. Polynucleotide molecules encoding proteins involved in herbicide tolerance are well-known in the art and include, but are not limited to, a polynucleotide molecule encoding 5-enolpyruvylshikimate-3-phosphate synthase (EPSPS) disclosed in U.S. Pat. Nos. 5,094,945; 5,627,061; 5,633,435 and 6,040,497 for imparting glyphosate tolerance; polynucleotide molecules encoding a glyphosate oxidoreductase (GOX) disclosed in U.S. Pat. No. 5,463,175 and a glyphosate-N-acetyl transferase (GAT) disclosed in US Patent Application Publication 2003/

0083480 A1 also for imparting glyphosate tolerance; dicamba monooxygenase disclosed in US Patent Application Publication 2003/0135879 A1 for imparting dicamba tolerance; a polynucleotide molecule encoding bromoxynil nitrilase (Bxn) disclosed in U.S. Pat. No. 4,810,648 for imparting bromoxynil tolerance; a polynucleotide molecule encoding phytoene desaturase (crtl) described in Misawa et al, (1993) Plant J. 4:833-840 and in Misawa et al, (1994) Plant J. 6:481-489 for norflurazon tolerance; a polynucleotide molecule encoding acetohydroxyacid synthase (AHAS, aka ALS) described in Sathasnvan et al. (1990) Nucl. Acids Res. 18:2188-2193 for imparting tolerance to sulfonylurea herbicides; polynucleotide molecules known as bar genes disclosed in DeBlock, et al. (1987) EMBO J. 6:2513-2519 for imparting glufosinate and bialaphos tolerance; polynucleotide molecules disclosed in US Patent Application Publication 2003/010609 A1 for imparting N-amino methyl phosphonic acid tolerance; polynucleotide molecules disclosed in U.S. Pat. No. 6,107,549 for imparting pyridine herbicide resistance; molecules and methods for imparting tolerance to multiple herbicides such as glyphosate, atrazine, ALS inhibitors, isoxoflutole and glufosinate herbicides are disclosed in U.S. Pat. No. 6,376,754 and US Patent Application Publication 2002/0112260. Molecules and methods for imparting insect/nematode/virus resistance are disclosed in U.S. Pat. Nos. 5,250,515; 5,880,275; 6,506, 599; 5,986,175 and US Patent Application Publication 2003/0150017 A1.

Plant Cell Transformation Methods

Numerous methods for transforming chromosomes in a plant cell nucleus with recombinant DNA are known in the art and are used in methods of preparing a transgenic plant cell nucleus, and plant. Two effective methods for such transformation are *Agrobacterium*-mediated transformation and microprojectile bombardment. Microprojectile bombardment methods are illustrated in U.S. Pat. No. 5,550,318 (corn); U.S. Pat. No. 5,538,880 (corn); U.S. Pat. No. 6,160, 208 (corn); U.S. Pat. No. 6,399,861 (corn); U.S. Pat. No. 6,153,812 (wheat) and U.S. Pat. No. 6,365,807 (rice) and *Agrobacterium*-mediated transformation is described in U.S. Pat. No. 5,591,616 (corn); U.S. Pat. No. 7,026,528 (wheat) and U.S. Pat. No. 6,329,571 (rice), all of which are incorporated herein by reference for enabling the production of transgenic plants. Transformation of plant material is practiced in tissue culture on a nutrient media, i.e. a mixture of nutrients that will allow cells to grow in vitro. Recipient cell targets include, but are not limited to, meristem cells, hypocotyls, calli, immature embryos and gametic cells such as microspores, pollen, sperm and egg cells. Callus may be initiated from tissue sources including, but not limited to, immature embryos, hypocotyls, seedling apical meristems, microspores and the like. Cells containing a transgenic nucleus are grown into transgenic plants.

In addition to direct transformation of a plant material with a recombinant DNA, a transgenic plant cell nucleus can be prepared by crossing a first plant having cells with a transgenic nucleus with recombinant DNA with a second plant lacking the transgenic nucleus. For example, recombinant DNA can be introduced into a nucleus from a first plant line that is amenable to transformation to transgenic nucleus in cells that are grown into a transgenic plant which can be crossed with a second plant line to introgress the recombinant DNA into the second plant line. A transgenic plant with recombinant DNA providing an enhanced trait, e.g. enhanced yield, can be crossed with a transgenic plant line having other recombinant DNA that confers another trait, for example herbicide resistance or pest resistance, to produce progeny plants having recombinant DNA that confers both traits. Typically, in such breeding for combining traits the transgenic plant donating the additional trait is a male line and the transgenic plant carrying the base traits is the female line. The progeny of this cross will segregate such that some of the plants will carry the DNA for both parental traits and some will carry DNA for one parental trait; such plants can be identified by markers associated with parental recombinant DNA, e.g. marker identification by analysis for recombinant DNA or, in the case where a selectable marker is linked to the recombinant DNA, by application of the selecting agent such as a herbicide for use with a herbicide tolerance marker, or by selection for the enhanced trait. Progeny plants carrying DNA for both parental traits can be crossed back into the female parent line multiple times, for example usually 6 to 8 generations, to produce a progeny plant with substantially the same genotype as one original transgenic parental line but for the recombinant DNA of the other transgenic parental line In the practice of transformation DNA is typically introduced into only a small percentage of target plant cells in any one transformation experiment. Marker genes are used to provide an efficient system for identification of those cells that are stably transformed by receiving and integrating a recombinant DNA molecule into their genomes. Preferred marker genes provide selective markers which confer resistance to a selective agent, such as an antibiotic or a herbicide. Any of the herbicides to which plants of this invention may be resistant are useful agents for selective markers. Potentially transformed cells are exposed to the selective agent. In the population of surviving cells will be those cells where, generally, the resistance-conferring gene is integrated and expressed at sufficient levels to permit cell survival. Cells may be tested further to confirm stable integration of the exogenous DNA. Commonly used selective marker genes include 'those conferring resistance to antibiotics such as kanamycin and paromomycin (nptll), hygromycin B {aph W), spectinomycin (aadA) and gentamycin (aac3 and aacCA) or resistance to herbicides such as glufosinate {bar or pat), dicamba (DMO) and glyphosate (aroA or EPSPS). Examples of such selectable markers are illustrated in U.S. Pat. Nos. 5,550,318; 5,633,435; 5,780,708 and 6,118,047. Markers which provide an ability to visually screen transformants can also be employed, for example, a gene expressing a colored or fluorescent protein such as a luciferase or green fluorescent protein (GFP) or a gene expressing a føtø-glucuronidase or uidA gene (GUS) for which various chromogenic substrates are known.

Plant cells that survive exposure to the selective agent, or plant cells that have been scored positive in a screening assay, may be cultured in regeneration media and allowed to mature into plants. Developing plantlets regenerated from transformed plant cells can be transferred to plant growth mix, and hardened off, for example, in an environmentally controlled chamber at about 85% relative humidity, 600 ppm $CO_2$, and 25-250 microeinsteins $m^{'2}$ $s^{'1}$ of light, prior to transfer to a greenhouse or growth chamber for maturation. Plants are regenerated from about 6 weeks to 10 months after a transformant is identified, depending on the initial tissue, and plant species. Plants may be pollinated using conventional plant breeding methods known to those of skill in the art and seed produced, for example self-pollination is commonly used with transgenic corn. The regenerated transformed plant or its progeny seed or plants can be tested for expression of the recombinant DNA and selected for the presence of enhanced agronomic trait.

Transgenic Plants and Seeds

Transgenic plants derived from transgenic plant cells having a transgenic nucleus of this invention are grown to generate transgenic plants having an enhanced trait as compared to a control plant and produce transgenic seed and haploid pollen of this invention. Such plants with enhanced traits are identified by selection of transformed plants or progeny seed for the enhanced trait. For efficiency a selection method is designed to evaluate multiple transgenic plants (events) comprising the recombinant DNA, for example multiple plants from 2 to 20 or more transgenic events. Transgenic plants grown from transgenic seed provided herein demonstrate improved agronomic traits that contribute to increased yield or other trait that provides increased plant value, including, for example, improved seed quality. Of particular interest are plants having enhanced water use efficiency, enhanced cold tolerance, increased yield, enhanced nitrogen use efficiency, enhanced seed protein and enhanced seed oil.

Transgenic crops containing insect resistance (IR) traits are prevalent in corn and cotton plants throughout North America, and usage of these traits is expanding globally. Commercial transgenic crops combining IR and herbicide tolerance (HT) traits have been developed by multiple seed companies. These include combinations of IR traits conferred by B.t. (*Bacillus thuringiensis*) insecticidal proteins and HT traits such as tolerance to Acetolactate Synthase (ALS) inhibitors such as Sulfonylureas, Imidazolinones, Triazolopyrimidine, Sulfonanilides, and the like, Glutamine Synthetase (GS) inhibitors such as Bialaphos, Glufosinate, and the like, 4-HydroxyPhenylPyruvate Dioxygenase (HPPD) inhibitors such as Mesotrione, Isoxaflutole, and the like, 5-EnolPyruvylShikimate-3-Phosphate Synthase (EPSPS) inhibitors such as Glyphosate and the like, and Acetyl-Coenzyme A Carboxylase (ACCase) inhibitors such as Haloxyfop, Quizalofop, Diclofop, and the like. Other examples are known in which transgenically provided proteins provide plant tolerance to herbicide chemical classes such as phenoxy acids herbicides and pyridyloxyacetates auxin herbicides (see WO 2007/053482 A2), or phenoxy acids herbicides and aryloxyphenoxypropionates herbicides (see WO 2005107437 A2, A3).

The ability to control multiple pest problems through various traits is a valuable commercial product concept, and the convenience of this product concept is enhanced if insect control traits and/or weed control traits and/or agronomic traits are combined in the same plant. Further, improved value may be obtained via single plant combinations of IR traits conferred by a B.t. insecticidal protein with one or more additional HT traits such as those mentioned above, plus one or more additional input traits (e.g. other insect resistance conferred by B.t.-derived or other insecticidal proteins, insect resistance conferred by mechanisms such as RNAi and the like, disease resistance, stress tolerance, improved nitrogen utilization, and the like), or output traits (e.g. high oils content, healthy oil composition, nutritional improvement, and the like). Such combinations may be obtained either through conventional breeding (e.g. breeding stack) or jointly as a novel transformation event involving the simultaneous introduction of multiple genes (e.g. molecular stack). Such stacking may be performed using RNAi technology or through the use of EXZACT®. Co-transformation of genes can be carried out using single transformation vectors comprising multiple genes or genes carried separately on multiple vectors. Benefits include the ability to manage insect pests and improved weed control in a crop plant that provides secondary benefits to the producer and/or the consumer. Thus, the subject invention can be used to provide transformed plants with combinations of traits that comprise a complete agronomic package of improved crop quality with the ability to flexibly and cost effectively control any number of agronomic issues.

Likewise, by means of the present invention, agronomic genes can be expressed in plants of the present invention. More particularly, plants can be genetically engineered to express various phenotypes of agronomic interest. Exemplary genes implicated in this regard include, but are not limited to, those categorized below:

1. Genes that Confer Resistance to Pests or Disease and that Encode:

A. Plant disease resistance genes. Plant defenses are often activated by specific interaction between the product of a disease resistance gene (R) in the plant and the product of a corresponding avirulence (Avr) gene in the pathogen. A plant variety can be transformed with cloned resistance genes to engineer plants that are resistant to specific pathogen strains. See, for example, Jones et al., Science 266:789 (1994) (cloning of the tomato Cf-9 gene for resistance to *Cladosporium fulvum*); Martin et al., Science 262:1432 (1993) (tomato Pto gene for resistance to *Pseudomonas syringae* pv. tomato encodes a protein kinase); Mindrinos et al., Cell 78:1089 (1994) (*Arabidopsis* RSP2 gene for resistance to *Pseudomonas syringae*).

B. A gene conferring resistance to a pest, such as soybean cyst nematode. See e.g., PCT Application WO 96/30517; PCT Application WO 93/19181.

C. A *Bacillus thuringiensis* protein, a derivative thereof or a synthetic polypeptide modeled thereon. See, for example, Geiser et al., Gene 48:109 (1986), who disclose the cloning and nucleotide sequence of a Bt .delta.-endotoxin gene. Moreover, DNA molecules encoding .delta.-endotoxin genes can be purchased from American Type Culture Collection, Manassas, Va., for example, under ATCC Accession Nos. 40098, 67136, 31995 and 31998.

D. A lectin. See, for example, the disclosure by Van Damme et al., Plant Molec. Biol. 24:25 (1994), who disclose the nucleotide sequences of several *Clivia miniata* mannose-binding lectin genes.

E. A vitamin-binding protein such as avidin. See PCT application US93/06487. The application teaches the use of avidin and avidin homologues as larvicides against insect pests.

F. An enzyme inhibitor, for example, a protease or proteinase inhibitor or an amylase inhibitor. See, for example, Abe et al., J. Biol. Chem. 262:16793 (1987) (nucleotide sequence of rice cysteine proteinase inhibitor); Huub et al., Plant Molec. Biol. 21:985 (1993) (nucleotide sequence of cDNA encoding tobacco proteinase inhibitor I); Sumitani et al., Biosci. Biotech. Biochem. 57:1243 (1993) (nucleotide sequence of *Streptomyces nitrosporeus* .alpha.-amylase inhibitor); and U.S. Pat. No. 5,494,813 (Hepher and Atkinson, issued Feb. 27, 1996).

G. An insect-specific hormone or pheromone such as an ecdysteroid or juvenile hormone, a variant thereof, a mimetic based thereon, or an antagonist or agonist thereof. See, for example, the disclosure by Hammock et al., Nature 344:458 (1990), of baculovirus expression of cloned juvenile hormone esterase, an inactivator of juvenile hormone.

H. An insect-specific peptide or neuropeptide which, upon expression, disrupts the physiology of the affected pest. For example, see the disclosures of Regan, J. Biol. Chem. 269:9 (1994) (expression cloning yields DNA coding for insect diuretic hormone receptor); and Pratt et al., Biochem. Biophys. Res. Comm. 163:1243 (1989) (an allostatin is identified in *Diploptera puntata*). See also U.S. Pat. No. 5,266,317 to Tomalski et al., who disclose genes encoding insect-specific, paralytic neurotoxins.

I. An insect-specific venom produced in nature by a snake, a wasp, etc. For example, see Pang et al., Gene 116:165 (1992), for disclosure of heterologous expression in plants of a gene coding for a scorpion insectotoxic peptide.

J. An enzyme responsible for a hyperaccumulation of a monoterpene, a sesquiterpene, a steroid, hydroxamic acid, a phenylpropanoid derivative or another non-protein molecule with insecticidal activity.

K. An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See PCT application WO 93/02197 in the name of Scott et al., which discloses the nucleotide sequence of a callase gene. DNA molecules which contain chitinase-encoding sequences can be obtained, for example, from the ATCC under Accession Nos. 39637 and 67152. See also Kramer et al., Insect Biochem. Molec. Biol. 23:691 (1993), who teach the nucleotide sequence of a cDNA encoding tobacco hornworm chitinase; and Kawalleck et al., Plant Molec. Biol. 21:673 (1993), who provide the nucleotide sequence of the parsley ubi-4-2 polyubiquitin gene.

L. A molecule that stimulates signal transduction. For example, see the disclosure by Botella et al., Plant Molec. Biol. 24:757 (1994), of nucleotide sequences for mung bean calmodulin cDNA clones; and Griess et al., Plant Physiol. 104:1467 (1994), who provide the nucleotide sequence of a maize calmodulin cDNA clone.

M. A hydrophobic moment peptide. See PCT application WO 95/16776 (disclosure of peptide derivatives of Tachyplesin which inhibit fungal plant pathogens) and PCT application WO 95/18855 (teaches synthetic antimicrobial peptides that confer disease resistance).

N. A membrane permease, a channel former or a channel blocker. For example, see the disclosure of Jaynes et al., Plant Sci. 89:43 (1993), of heterologous expression of a cecropin-.beta., lytic peptide analog to render transgenic tobacco plants resistant to *Pseudomonas solanacearum*.

O. A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See Beachy et al., Ann. rev. Phytopathol. 28:451 (1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

P. An insect-specific antibody or an immunotoxin derived therefrom. Thus, an antibody targeted to a critical metabolic function in the insect gut would inactivate an affected enzyme, killing the insect. Cf. Taylor et al., Abstract #497, Seventh Int'l Symposium on Molecular Plant-Microbe Interactions (Edinburgh, Scotland) (1994) (enzymatic inactivation in transgenic tobacco via production of single-chain antibody fragments).

Q. A virus-specific antibody. See, for example, Tavladoraki et al., Nature 366:469 (1993), who show that transgenic plants expressing recombinant antibody genes are protected from virus attack.

R. A developmental-arrestive protein produced in nature by a pathogen or a parasite. Thus, fungal endo .alpha.-1,4-D-polygalacturonases facilitate fungal colonization and plant nutrient release by solubilizing plant cell wall homo-.alpha.-1,4-D-galacturonase. See Lamb et al., Bio/Technology 10:1436 (1992). The cloning and characterization of a gene which encodes a bean endopolygalacturonase-inhibiting protein is described by Toubart et al., Plant J. 2:367 (1992).

S. A developmental-arrestive protein produced in nature by a plant. For example, Logemann et al., Bio/Technology 10:305 (1992), have shown that transgenic plants expressing the barley ribosome-inactivating gene have an increased resistance to fungal disease.

2. Genes that Confer Resistance to an Herbicide:

A. An herbicide that inhibits the growing point or meristem, such as an imidazolinone or a sulfonylurea. Exemplary genes in this category code for mutant ALS and AHAS enzyme as described, for example, by Lee et al., EMBO J. 7:1241 (1988); and Miki et al., Theon. Appl. Genet. 80:449 (1990), respectively.

B. Glyphosate (resistance conferred by, e.g., mutant 5-enolpyruvylshikimate-3-phosphate synthase (EPSPs) genes (via the introduction of recombinant nucleic acids and/or various forms of in vivo mutagenesis of native EPSPs genes), aroA genes and glyphosate acetyl transferase (GAT) genes, respectively), other phosphono compounds such as glufosinate (phosphinothricin acetyl transferase (PAT) genes from *Streptomyces* species, including *Streptomyces hygroscopicus* and *Streptomyces viridichromogenes*), and pyridinoxy or phenoxy proprionic acids and cyclohexones (AC-Case inhibitor-encoding genes), See, for example, U.S. Pat. No. 4,940,835 to Shah, et al. and U.S. Pat. No. 6,248,876 to Barry et. al., which disclose nucleotide sequences of forms of EPSPs which can confer glyphosate resistance to a plant. A DNA molecule encoding a mutant aroA gene can be obtained under ATCC accession number 39256, and the nucleotide sequence of the mutant gene is disclosed in U.S. Pat. No. 4,769,061 to Comai. European patent application No. 0 333 033 to Kumada et al., and U.S. Pat. No. 4,975,374 to Goodman et al., disclose nucleotide sequences of glutamine synthetase genes which confer resistance to herbicides such as L-phosphinothricin. The nucleotide sequence of a PAT gene is provided in European application No. 0 242 246 to Leemans et al., DeGreef et al., Bio/Technology 7:61 (1989), describe the production of transgenic plants that express chimeric bar genes coding for PAT activity. Exemplary of genes conferring resistance to phenoxy proprionic acids and cyclohexones, such as sethoxydim and haloxyfop are the Accl-S1, Accl-S2 and Accl-S3 genes described by Marshall et al., Theon. Appl. Genet. 83:435 (1992). GAT genes capable of conferring glyphosate resistance are described in WO 2005012515 to Castle et. al. Genes conferring resistance to 2,4-D, fop and pyridyloxy auxin herbicides are described in WO 2005107437 and U.S. patent application Ser. No. 11/587,893, both assigned to Dow AgroSciences LLC.

C. An herbicide that inhibits photosynthesis, such as a triazine (psbA and 1s+ genes) or a benzonitrile (nitrilase gene). Przibila et al., Plant Cell 3:169 (1991), describe the transformation of *Chlamydomonas* with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441, and 67442. Cloning and expression of DNA coding for a glutathione S-transferase is described by Hayes et al., Biochem. J. 285:173 (1992).

3. Genes that Confer or Contribute to a Value-Added Trait, Such as:

A. Modified fatty acid metabolism, for example, by transforming a plant with an antisense gene of stearyl-ACP desaturase to increase stearic acid content of the plant. See Knultzon et al., Proc. Natl. Acad. Sci. U.S.A. 89:2624 (1992).

B. Decreased phytate content—1) Introduction of a phytase-encoding gene would enhance breakdown of phytate, adding more free phosphate to the transformed plant. For example, see Van Hartingsveldt et al., Gene 127:87 (1993), for a disclosure of the nucleotide sequence of an *Aspergillus niger* phytase gene. 2) A gene could be introduced that reduced phytate content. In maize for example, this could be accomplished by cloning and then reintroducing DNA associated with the single allele which is responsible for maize mutants characterized by low levels of phytic acid. See Raboy et al., Maydica 35:383 (1990).

C. Modified carbohydrate composition effected, for example, by transforming plants with a gene coding for an enzyme that alters the branching pattern of starch. See Shiroza et al., J. Bacteol. 170:810 (1988) (nucleotide sequence of *Streptococcus* mutants fructosyltransferase gene); Steinmetz et al., Mol. Gen. Genet. 20:220 (1985) (nucleotide sequence of *Bacillus subtilis* levansucrase gene); Pen et al., Bio/Technology 10:292 (1992) (production of transgenic plants that express *Bacillus licheniformis* .alpha.-amylase); Elliot et al., Plant Molec. Biol. 21:515 (1993) (nucleotide sequences of tomato invertase genes); Sogaard et al., J. Biol. Chem. 268:22480 (1993) (site-directed mutagenesis of barley .alpha.-amylase gene); and Fisher et al., Plant Physiol. 102:1045 (1993) (maize endosperm starch branching enzyme II).

D. Abiotic Stress Tolerance which includes resistance to non-biological sources of stress conferred by traits such as nitrogen utilization efficiency, altered nitrogen responsiveness, drought resistance cold, and salt resistance. Genes that affect abiotic stress resistance (including but not limited to flowering, ear and seed development, enhancement of nitrogen utilization efficiency, altered nitrogen responsiveness, drought resistance or tolerance, cold resistance or tolerance, and salt resistance or tolerance) and increased yield under stress.

The expression of isolated nucleic acids encoding a protein of the present invention can be achieved by operably linking, for example, the DNA or cDNA to a promoter (which is either constitutive or regulatable), followed by incorporation into an expression vector. The vectors can be suitable for replication and integration in either prokaryotes or eukaryotes. Typical expression vectors contain transcription and translation terminators, initiation sequences, and promoters useful for regulation of the expression of the DNA encoding a protein of the present invention. To obtain high level expression of a cloned gene, it is desirable to construct expression vectors which contain, at the minimum, a promoter to direct transcription, a ribosome binding site for translational initiation, and a transcription/translation terminator. One of skill will recognize that modifications can be made to a protein of the present invention without diminishing its biological activity. Some modifications can be made to facilitate the cloning, expression, or incorporation of the targeting molecule into a fusion protein. Such modifications are well known to those of skill in the art and include, for example, a methionine added at the amino terminus to provide an initiation site, or additional amino acids (e.g., poly His) placed on either terminus to create conveniently located purification sequences. Restriction sites or termination codons can also be introduced.

Prokaryotic cells can be used as hosts for expression. Prokaryotes most frequently are represented by various strains of *E. coli*; however, other microbial strains can also be used. Commonly used prokaryotic control sequences which are defined herein to include promoters for transcription initiation, optionally with an operator, along with ribosome binding site sequences, include such commonly used promoters as the beta lactamase (penicillinase) and lactose (lac) promoter systems (Chang et al., Nature 198:1056 (1977)), the tryptophan (trp) promoter system (Goeddel et al., Nucleic Acids Res. 8:4057 (1980)) and the lambda derived P L promoter and N-gene ribosome binding site (Shimatake et al., Nature 292:128 (1981)). The inclusion of selection markers in DNA vectors transfected in *E. coli* is also useful. Examples of such markers include genes specifying resistance to ampicillin, tetracycline, or chloramphenicol.

The vector is selected to allow introduction into the appropriate host cell. Bacterial vectors are typically of plasmid or phage origin. Appropriate bacterial cells are infected with phage vector particles or transfected with naked phage vector DNA. If a plasmid vector is used, the bacterial cells are transfected with the plasmid vector DNA. Expression systems for expressing a protein of the present invention are available using *Bacillus* sp. and *Salmonella* (Palva et al., Gene 22:229-235 (1983); Mosbach et al., Nature 302:543-545 (1983)).

The proteins of this invention, recombinant or synthetic, can be purified to substantial purity by standard techniques well known in the art, including detergent solubilization, selective precipitation with such substances as ammonium sulfate, column chromatography, immunopurification methods, and others. See, for instance, R. Scopes, Protein Purification: Principles and Practice, Springer-Verlag: New York (1982); Deutscher, Guide to Protein Purification, Academic Press (1990). For example, antibodies can be raised to the proteins as described herein. Purification from *E. coli* can be achieved following procedures described in U.S. Pat. No. 4,511,503. The protein can then be isolated from cells expressing the protein and further purified by standard protein chemistry techniques as described herein.

The present invention provides methods for expressing a plurality of enzyme activities through the use of gene fusion constructs or chimeric DNAs, as well as methods for producing modified gene constructs. In addition, the present invention provides the gene fusion constructs for use in these methods, and the modified gene fusion constructs prepared by these methods. Gene fusion constructs in their simplest form are combinations of nucleic acid sequences encoding enzymatic domains. The constructs can further include nucleic acid sequences that participate in expression of the encoded hybrid protein, such as transcription elements, promoters, termination sequences, introns, and the like. In addition, the constructs can include nucleotide linker sequences such as those described below.

The nucleic acid sequences cojoined to form the gene fusion constructs and modified gene fusion constructs of the present invention can be various forms of deoxyribonucleic acid (for example, genomic DNA, cDNA, sense-strand sequences, antisense-strand sequences, recombinant DNA, shuffled DNA, modified DNA, or DNA analogs). Alternatively, the nucleic acid sequences can be ribonucleic acid (including, but not limited to, genomic RNA, messenger RNA, catalytic RNA, sense-strand sequences, antisense-strand sequences, recombinant RNA, shuffled RNA, modified RNA, or RNA analogs). The nucleic acid sequences incorporated into the fusion constructs of the present invention can also be derived from one or more libraries of nucleic acid sequences.

The gene fusion constructs and modified gene fusion constructs of the present invention can be prepared by a number of techniques known in the art, such as molecular cloning techniques. A wide variety of cloning and in vitro amplification methods suitable for the construction of recombinant nucleic acids, such as expression vectors, are well-known to persons of skill. General texts which describe molecular biological techniques useful herein, including mutagenesis, include Berger and Kimmel, Guide to Molecular Cloning Techniques, Methods in Enzymology, volume 152 Academic Press, Inc., San Diego, Calif. ("Berger"); Sambrook, et al., Molecular Cloning—A Laboratory Manual (2nd Ed.), volumes 1-3, Cold Spring Harbor Laboratory, Cold Spring Harbor, N.Y., 1989 ("Sambrook"); and Current Protocols in Molecular Biology, F. M. Ausubel, et al., eds., Current Protocols, a joint venture between Greene Publishing Associates, Inc. and John Wiley & Sons, Inc., (supplemented through 2000) ("Ausubel")). Examples of techniques sufficient to direct persons of skill through in vitro amplification methods, including the polymerase chain reaction (PCR) the ligase chain reaction (LCR), Q.beta.-replicase amplification and other RNA polymerase mediated techniques (e.g., NASBA) are found in Berger, Sambrook, and Ausubel, as well as Mullis, et al., (1987) U.S. Pat. No. 4,683,202; PCR Protocols A Guide to Methods and Applications (Innis, et al., eds.) Academic Press Inc. San Diego, Calif. (1990); Arnheim & Levinson (Oct. 1, 1990) Chemical and Engineering News 36-47; The Journal Of NIH Research (1991) 3:81-94; Kwoh, et al., (1989) Proc Natl Acad. Sci. USA 86:1173; Guatelli, et al., (1990) Proc Natl Acad Sci USA 87:1874; Lomell, et al., (1989) J Clin Chem 35:1826; Landegren, et al., (1988) Science 241:1077-1080; Van Brunt (1990) Biotechnology 8:291-294; Wu and Wallace, (1989) Gene 4:560; Barringer, et al., (1990) Gene 89:117, and Sooknanan and Malek (1995) Biotechnology 13:563-564. Improved methods of cloning in vitro amplified nucleic acids are described in Wallace, et al., U.S. Pat. No. 5,426,039. Improved methods of amplifying large nucleic acids by PCR are summarized in Cheng, et al., (1994) Nature 369: 684-685 and the references therein, in which PCR amplicons of up to 40 kb are generated. One of skill will appreciate that essentially any RNA can be converted into a double stranded DNA suitable for restriction digestion, PCR expansion and sequencing using reverse transcriptase and a polymerase. See, Ausbel, Sambrook and Berger, all supra.

Detection of the expressed protein in all in vivo systems is achieved by methods known in the art and include, for example, radioimmunoassays, Western blotting techniques or immunoprecipitation.

The present invention relates to mechanisms for expressing a really interesting new gene (RING) which is a protein with a structural domain of a zinc finger type which generally has a consensus sequence of C—$X_2$—C—$X_{[9-39]}$—C—$X_{[1-3]}$—H—$X_{[2-3]}$—C—$X_2$—C—$X_{[4-48]}$—C—$X_2$—C. (SEQ ID NO: 4)

While the invention has been described with reference to specific methods and embodiments, it will be appreciated that various modifications and changes may be made without departing from the invention. All publications cited herein are expressly incorporated herein by reference for the purpose of describing and disclosing compositions and methodologies that might be used in connection with the invention. All cited patents, patent applications, and sequence information in referenced websites and public databases are also incorporated by reference.

EXAMPLE 1

Three hybrids derived from BS112, SLM03, SLM02 and 7SH382 were planted at Fresno Calif. in 2006. Two water treatments (control and 20% watering) were imposed on two repeated plots. Three leaf samples were collected from each plot at flowering for microarray experiments.

Based on the kernel number per plants, the hybrids were classified into two groups: drought tolerant hybrids (DASDTC1, DASDTC2) and drought susceptible hybrid (DASDTC3). Six microarray hybridizations were conducted with three pairs of dye-swaps using probes synthesized from mRNA from the leaf tissues.

Microarray experiments were performed using 57,000 70 mer oligos synthesized by Operon Technologies. The oligos were designed by the Maize Oligo Microarray Consortium Leading by University of Arizona. The microarray slides were fabricated at Dow AgroSciences using an microarray array robot (OminiGird, GeneMachine). Genes that were differentially expressed under drought condition with confidence of $P<0.05$ were selected using Genowiz program. Genes that were differentially expressed in both of the drought tolerant hybrids, but not in the drought sensitive hybrid were selected with Venn Diagram.

Under drought treatment, 4,334 genes were differentially expressed in (DASDTC1, DASDTC2) genes were differentially expressed in SLMO3/BS112. A total of 3,423 genes were differentially expressed in drought sensitive hybrid SLM02/BS112.

A total of 99 genes were up-regulated in both of the drought tolerant hybrids (DASDTC1, DASDTC2), but not in the drought susceptible hybrid DASDTC3. ZmRING is among the 99 up-regulated genes.

EXAMPLE 2

Codon Optimization of Protein Coding Sequences for Plant Expression

In a preferred embodiment of the present disclosure, plants were transformed with genes wherein the codon usage of the protein coding region has been optimized for expression in plants. See, for example, U.S. Pat. No. 5,380,831, which is hereby incorporated by reference. A DNA sequence having a plant codon bias was designed and synthesized to produce a ZmRING protein (SEQ ID NO. 2) in transgenic monocot plants. A codon usage table for maize (*Zea mays* L.) was calculated from 706 protein coding sequences (CDS) obtained from sequences deposited in GENBANK™. A biased codon set that comprises frequently used codons common to both maize and other monocot datasets, in appropriate rescaled average relative amounts, was calculated after omitting any redundant codon used less than about 10% of total codon uses for that amino acid in either plant type. A plant optimized sequence encoding a ZmRING protein (SEQ ID NO:2) was derived by making codon substitutions to the experimentally determined ZmRING sequence disclosed as SEQ ID NO:1 (obtained by combining transcripts and genomic sequences from maize inbred line B73), such that the resulting DNA sequence had the overall codon composition of the plant-optimized codon bias table. Further refinements of the sequence were made to eliminate undesirable restriction enzyme recognition sites, potential plant intron splice sites, long runs of A/T or C/G residues, and other motifs that might interfere with RNA stability, transcription, or translation of the coding region in plant cells. Other changes were made to introduce desired restriction enzyme recognition sites, and to eliminate long internal Open Reading Frames (frames other than +1). These changes were all made within the constraints of retaining the plant-biased codon composition. Synthesis of the designed sequence was performed by a commercial vendor (DNA2.0, Menlo Park, Calif.).

Additional guidance regarding the production of synthetic genes can be found in, for example, WO 97/13402, U.S. Pat. No. 6,166,302 and U.S. Pat. No. 5,380,831.

A plant-optimized DNA sequence encoding a full length ZmRING protein is disclosed as SEQ ID NO:3.

EXAMPLE 3

Agrobacterium Transformation for Generation of Maize Transformation Vector

The *Agrobacterium* superbinary system is conveniently used for transformation of monocot plant hosts. Methodologies for constructing and validating superbinary vectors are well disclosed and incorporated herein by reference (*Operating Manual for Plasmid pSB1*, Version 3.1, available from Japan Tobacco, Inc., Tokyo, Japan). Standard molecular biological and microbiological methods were used to generate superbinary plasmids. Verification/validation of the structure of the superbinary plasmid was done using methodologies as suggested in the Operating Manual for PlasmidpSB1. Table 1 discloses and describes the superbinary plasmid used in this work.

TABLE 1

Descriptions of plasmids.

| Plasmid | Description |
| --- | --- |
| pEPS1004 | Superbinary vector formed by co-integration of pSB1 and pDAB8107, a modified version of pSB11. |
| pDAB8107 | pSB11-based shuttle vector that harbors a plant selectable marker/herbicide tolerance gene comprising an aad1 coding region driven by a rice actin1 promoter with associated intron 1 and terminated by a maize lipase 3'UTR. Further harbors ZmRING coding region (SEQ ID NO: 3) driven by a maize ubiquitin1 promoter with associated intron1 and terminated by a maize Per5 3'UTR. |

Modified versions of the plasmid pSB11 shuttle vector, which is a component of the superbinary system, were constructed by standard molecular cloning methods in combination with manipulations exploiting the GATEWAY™ system (INVITROGEN, Carlsbad, Calif.) as appropriate. In one exemplification (e.g. plasmid pDAB8107), expression in maize cells of the coding region for an aad1 selectable marker/herbicide tolerance gene (disclosed in U.S. Pat. No. 7,838,733) was driven by a rice actin1 promoter and associated intron 1 essentially as disclosed in U.S. Pat. No. 5,641,876 and GENBANK™ Accession No. EU155408.1, and transcription of a plant-optimized coding region (SEQ ID NO:3) for a ZmRING protein was driven by a maize ubiquitin1 promoter and associated intron 1 as disclosed in U.S. Pat. No. 5,510,474 and GENBANK™ Accession No. S94464.1. Termination of transcription and polyadenylation of the aad1 mRNAs were specified by a maize lipase 3'UTR, essentially as disclosed as bases 921 to 1277 of GENBANK™ Accession No. gb|L35913.1|MZELIPASE and in U.S. Pat. No. 7,179,902, and these operations for the mRNAs of the ZmRING gene of this disclosure were specified by a copy of the maize Per5 3'UTR as disclosed in U.S. Pat. No. 6,384,207.

The pSB11-derived shuttle vector pDAB8107 was introduced into the superbinary strain LBA4404(pSB1) by standard methods to produce the superbinary plasmid pEPS1004.

In another exemplification, transformation of maize is accomplished by means of a binary vector delivered by strains of *Agrobacterium tumefaciens*. Methods for transformation of maize by means of *Agrobacterium* strains harboring binary vectors are disclosed for example, by Oltmanns et al. (2010, Plant Physiol. 152:1158-1166). One skilled in the field of plant transformation will understand that several exemplifications of binary vectors are available for use, but all share a common set of characteristics, summarized as: a bacterial broad host range origin of plasmid replication capable of chromosome-independent replication in *Escherichia coli* and *Agrobacterium* cells; a bacterial selectable marker gene (usually one that confers antibiotic resistance); at least one, but usually two, T-DNA border repeat sequences that flank sequences such as multiple cloning sites for restriction enzymes or GATEWAY™ att sites into which genes destined for plant expression may be introduced. It is further commonly found that a binary vector contains sequences that enable conjugal transfer of the plasmid between bacterial cells.

Binary vectors may be constructed by standard molecular cloning methods in combination with manipulations exploiting the GATEWAY™ system as appropriate. In one exemplification, expression in maize cells of the coding region for an aad1 selectable marker/herbicide tolerance gene and the plant-optimized coding region for the ZmRING gene of this disclosure (SEQ ID NO:3) are both driven by independent copies of a ubiquitin promoter and associated intron 1. Termination of transcription and polyadenylation of the aad1 mRNAs are specified by a maize lipase 3'UTR, and these operations for the mRNAs of the ZmRING gene of this invention are specified by a copy of the maize Per5 3'UTR. Table 1 summarizes the pertinent gene compositions of the plasmids used in this work.

EXAMPLE 4

*Agrobacterium*-Mediated Transformation of Maize with Superbinary Vector pEPS1004

All temperatures in this and subsequent examples are given in degrees Celsius.

Immature Embryo Production

Seeds from inbred line, B104 (an Iowa State University variety commercially released in the early 1980's), were planted into 4-gallon-pots containing SUNSHINE CUSTOM BLEND 160 (SUN GRO HORTICULTURE; Bellevue, Wash.). The plants were grown in a greenhouse using a combination of high pressure sodium and metal halide lamps with a 16:8 hour Light:Dark photoperiod. To obtain immature embryos for transformation, controlled sib-pollinations were performed. Immature embryos were isolated at 10 to 13 days post-pollination when embryos were approximately 1.4 to 2.0 mm in size.

Infection and Co-Cultivation

Maize ears were surface sterilized by immersing in 50% commercial bleach with Tween 20 (1 or 2 drops per 500 mL) for 10 minutes and triple-rinsed with sterile water. A suspension of *Agrobacterium* cells containing superbinary vector pEPS1004 was prepared from bacteria grown on YEP solid medium containing 100 mg/L Spectinomycin, 10 mg/L Tetracycline, and 250 mg/L Streptomycin at 280 for 3 days or 25° for 4 days. One or 2 loopfuls of cells scraped from the plate were transferred into 5 mL of liquid infection medium comprising: MS salts (Frame et al., 2011, Genetic Transformation Using Maize Immature Zygotic Embryos. In Plant Embryo Culture Methods and Protocols: Methods in Molecular Biology. T. A. Thorpe and E. C. Yeung, (Eds), Springer Science and Business Media, LLC. pp 327-341), ISU Modified MS Vitamins (Frame et al., supra), 3.3 mg/L Dicamba-KOH, 68.4 gm/L sucrose, 36 gm/L glucose, 700 mg/L L-proline, pH 5.2, containing 100 µM acetosyringone. The solution was gently pipetted up and down using a sterile 5 mL pipette until a uniform suspension was achieved, and the concentration was adjusted to an optical density of 0.3 to 0.5 at 600 nm ($OD_{600}$) using an ULTROSPEC 10 CELL DENSITY METER (GE HEALTHCARE/AMERSHAM BIOSCIENCES; Piscataway, N.J.).

Co-Cultivation

Immature embryos were isolated directly into a micro centrifuge tube containing 2 mL of the infection medium. The medium was removed and replaced twice with 1 to 2 mL of fresh infection medium, then removed and replaced with 1.5 mL of the *Agrobacterium* solution. The *Agrobacterium* and embryo solution was incubated for 5 minutes at room temperature and then transferred to co-cultivation medium which contained MS salts, ISU Modified MS Vitamins, 3.3 mg/L Dicamba-KOH, 30 gm/L sucrose, 700 mg/L L-proline, 100 mg/L myo-inositol, 100 mg/L Casein Enzymatic Hydrolysate, 15 mg/L $AgNO_3$, 100 M acetosyringone, and 2.3 to 3 gm/L GELZAN™ (SIGMA-ALDRICH; St. Louis, Mo.), at pH 5.8. Co-cultivation incubation was for 3 to 4 days at 250 under either dark or 24-hour white fluorescent light conditions (approximately 50 $\mu Em^{-2} s^{-1}$).

Resting and Selection

After co-cultivation, the embryos were transferred to a non-selection MS-based resting medium containing MS salts, ISU Modified MS Vitamins, 3.3 mg/L Dicamba-KOH, 30 gm/L sucrose, 700 mg/L L-proline, 100 mg/L myo-inositol, 100 mg/L Casein Enzymatic Hydrolysate, 15 mg/L $AgNO_3$, 0.5 gm/L MES (2-(N-morpholino)ethanesulfonic acid monohydrate; PHYTOTECHNOLOGIES LABR.; Lenexa, Kans.), 250 mg/L Carbenicillin, and 2.3 gm/L GELZAN™, at pH 5.8. Incubation was continued for 7 days at 280 under either dark or 24-hour white fluorescent light conditions (approximately 50 $Em^{-2} s^{-1}$). Following the 7 day resting period, the embryos were transferred to selective medium. For selection of maize tissues transformed with a superbinary plasmid containing a plant expressible aad1 selectable marker gene, the MS-based resting medium (above) was used supplemented with Haloxyfop. The embryos were first transferred to selection media containing 100 nM Haloxyfop and incubated for 1 to 2 weeks, and then transferred to 500 nM Haloxyfop and incubated for an additional 2 to 4 weeks. Transformed isolates were obtained over the course of approximately 5 to 8 weeks at 280 under either dark or 24-hour white fluorescent light conditions (approximately 50 $Em^{-2} s^{-1}$). Recovered isolates were bulked up by transferring to fresh selection medium at 1 to 2 week intervals for regeneration and further analysis.

Those skilled in the art of maize transformation will understand that other methods of selection of transformed plants are available when other plant expressible selectable marker genes (e.g. herbicide tolerance genes) are used.

Pre-Regeneration

Following the selection process, cultures exposed to the 24-hour light regime were transferred to an MS-based pre-regeneration medium containing MS salts, ISU Modified MS Vitamins, 45 gm/L sucrose, 350 mg/L L-proline, 100 mg/L myo-inositol, 50 mg/L Casein Enzymatic Hydrolysate, 1 mg/L $AgNO_3$, 0.25 gm/L MES, 0.5 mg/L naphthalene acetic acid, 2.5 mg/L abscisic acid, 1 mg/L benzyladenine, 250 mg/L Carbenicillin, 2.5 gm/L GELZAN™, and 500 nM Haloxyfop, at pH 5.8. Incubation was continued for 7 days at 28° under 24-hour white fluorescent light conditions (approximately 50 $Em^{-2} s^{-1}$).

Regeneration and Plantlet Isolation

For regeneration, the cultures were transferred to an MS-based primary regeneration medium containing MS salts, ISU Modified MS Vitamins, 60 gm/L sucrose, 100 mg/L myo-inositol, 125 mg/L Carbenicillin, 2.5 gm/L GELZAN™, and 500 nM Haloxyfop, at pH 5.8. After 2 weeks at 280 under either dark or 24-hour white fluorescent light conditions (approximately 50 $Em^{-2} s^{-1}$), tissues were transferred to an MS-based secondary regeneration medium composed of MS salts, ISU Modified MS Vitamins, 30 gm/L sucrose, 100 mg/L myo-inositol, 3 gm/L GELZAN™, at pH 5.8, with, or without, 500 nM Haloxyfop. Regeneration/selection was continued for 2 weeks at 280 under either 16-hour or 24-hour white fluorescent light conditions (approximately 50 $Em^{-2} s^{-1}$). When plantlets reached 3 to 5 cm in length, they were excised and transferred to secondary regeneration medium (as above, but without Haloxyfop) and incubated at 250 under 16-hour white fluorescent light conditions (approximately 50 $Em^{-2} s^{-1}$) to allow for further growth and development of the shoot and roots.

Seed Production

Plants were transplanted into METRO-MIX 360 soilless growing medium (SUN GRO HORTICULTURE) and hardened-off in a growth room. Plants were then transplanted into SUNSHINE CUSTOM BLEND 160 soil mixture and grown to flowering in the greenhouse. Controlled pollinations for seed production were conducted.

EXAMPLE 5

Greenhouse Testing for Drought Tolerance

Transgenic maize plants that express the genes were tested in the greenhouse for their response to decreased water supply. Those skilled in the field of plant testing will understand that other methods of examining the drought tolerance of plants are available. It is to be understood that the methods disclosed herein are not meant to be limiting, and other methods of testing are intended to be within the scope of this invention.

Transgenic pEPS1004 T0 events in the B104 genetic background were crossed with non-transgenic B104 parents to produce segregating hemizygous transgenic lines. Test results for the plants of the transgenic lines were compared to those obtained with nontransgenic plants of parent variety B104 and also with a known drought-tolerant (nontransgenic) maize variety (DASDT69).

Plants were evaluated for several physiological parameters during a progressive dry down experiment wherein a portion of the water transpired each day was re-supplied such that plants were drying down gradually over the course of the experiment. The physiological parameters measured were the Transpiration Reduction Point (TRP) (Sinclair and Ludlow, 1986, Austral. J. Plant Physiol. 13:329-341), measured in terms of the fraction of transpirable moisture remaining in the soil, the Relative Leaf Surface Temperature (RLST) (Bolanos et al., 1993, Field Crops Res. 31:269-286) and the quantum yield of photosystem II (QY) (Selmani and Wassom, 1993, Field Crops Res. 31:173-184). The weight of individual PVC pots was recorded prior to them being filled with 3500 gm of planting soil comprising TOP SOIL BLEND obtained from a local nursery, mixed 1:1 (v:v) with PRO-MIX® HP and supplemented with 20 gms of OSMO-COTE® Plus 15-9-12 four month extended release fertilizer. The soil was irrigated from above until the soil was saturated. Plantlets were transplanted into the pots and the pots were irrigated again. Pots with plants were allowed to drain overnight and were then weighed to obtain Drained Upper Limit value (DUL). After collecting the DUL, drain holes in the pot bottoms were sealed and the top of the pot was sealed around the plant stalk by wrapping with PRESS N SEAL SARAN® wrap to prevent loss of water other than through transpiration. After plants were acclimated to the new environment for 3 to 4 days, a drought treatment was initiated.

Pots containing experimental plants (7 or 10 events per transformation construct; 12 plants per event per treatment) were weighed once or twice per day (at the same time(s) each day). For the plants in the progressive dry-down treatment, water was applied to attain a progressive dry-down rate of 100 gm water loss per 24-hour period (once-a-day watering cycle) or 50 gm water loss per interval period (twice-a-day watering cycle). Seed-grown plantlets of the nontransgenic drought susceptible B104 line and drought tolerant inbred line DASDT69 were used as negative and positive control materials, respectively. Well watered experimental control plants were watered to maintain soil moisture at 90% of the water content at the DUL.

At the first signs of plant wilting (Stage 11 drought), daily measurements of quantum yield, leaf surface temperature and a leaf roll score were taken for approximately 5 days.

Data were calculated using the terms and equations in Table 2 and Table 3. Secondary parameter data collections included measurements in some or all of the categories tabulated in Table 4.

TABLE 2

Glossary of terms

| Equation Term | Definition |
|---|---|
| Field Capacity (FC) | Total amount of water that the soil can hold. Water content at Drained Upper Limit |
| Drained Upper Limit (DUL) | Total Pot Weight at the time when the soil has been oversaturated and allowed to drain overnight. |
| Pot Weight (PW) | Pot only mass (in gm) |
| Soil Weight (SW) | Dry soil only mass (in gm) |
| Water Content (WC) | Amount of water in the pot at any given time. |
| Total Pot Weight (TPW) | Pot Weight + Soil Weight + Water weight |
| Time Initial (Ti) | Time at beginning of time period |
| Time Final (Tf) | Time at end of time period |
| Daily Water Loss or Transpiration Water Loss (TWL) | Amount of water transpired by plant over the course of a defined time period. |
| Water Metered (WM) | Amount of water given to plant as a calculation of total water lost over specified time frame minus allowable water loss to induce specific drought condition. |
| Well-Watered (WW) | Plants maintained at optimal water conditions of 0.90 Field Capacity |
| Progressive Dry Down | 100 gm water loss per 24 hour period |
| Fresh Weight (FW) | Weight of sample immediately after harvest from plant |
| Dry Weight (DW) | Weight of sample after drying at 75° C. for 3 days |
| Turgid Weight (TW) | Weight of sample after soaking in water at 4° C. for 24 hours. |
| Total Selection Score | A numerical score is given to the key parameters measured in the screen. The primary measurement (TRP) is weighted more strongly than the secondary parameters (RLST, QY). Statistical significance is determined by $p < 0.05$, $\alpha = 0.05$ ($\alpha = 0.10$, for trends). A finding of no statistical difference is given a score of zero. |
| Yield Well-Watered (YWW) | Grain yield in field tests under well watered conditions. May be calculated for the test event ($YWW_{TE}$) or the Check ($YWW_{CH}$) |
| Yield Drought Stress (YDS) | Grain yield in field tests under drought stress conditions. May be calculated for the test events ($YDS_{TE}$) or the Check ($YDS_{CH}$) |
| Yield Protection | A measure of the advantage that a given gene provides to the transgenic under drought stress conditions, compared to the check. |

TABLE 3

Equations

| | |
|---|---|
| Re-water Calculation for 0.90 FC (Well-Watered) | $0.90 \times (DUL - SW - PW)$ |
| Re-water Calculation for Progressive Dry Down | $FC - (100\ ml \times (\#\text{of days from drought start date})) - WC$ |
| Relative Leaf Surface Temperature (RLST) | (Leaf Surface Temperature)/ (Average Leaf Surface Temperature of Respective Well-watered Plants) |
| Field Capacity (FC) | $FC = DUL - SW - PW$ |
| Water Content (WC) | $WC = TPW - SW - PW$ |
| Water Loss (WL) | $WL = (TPW\ at\ Ti) - (TPW\ at\ Tf) +$ (Amount of water added at Ti) |
| Relative Transpiration (RT) | RT = (Individual plant's Water Loss)/ (Average Water Loss for all Well-Watered plants within the respective group) |
| Normalized Relative Transpiration (NRT) | NRT = RT(each individual plant)/ (Average RT of the first 3 days after wrapping for each individual plant) |
| Fraction of Transpirable Soil Water (FTSW) | $(1 - DUL - \text{daily PW})/$ $(DUL - \text{Lower Limit PW})$ |
| Transpiration Reduction Point (TRP) | Data is pooled into a scatter plot of Normalized Transpiration Rate (NRT) graphed against the Fraction of Transpirable Soil Water (FTSW) for each plant subjected to drought treatment of the respective event. TRP is calculated by a 2-segmented linear model analysis |
| Transpiration Efficiency (TE) | TE = Total DW accumulated/ Total water consumed |
| Percent Relative Water Content (RWC) | $RWC = [(FW - DW)/(TW - DW)] \times 100$ |
| Yield Loss (YL; bu/ac) | $YL = YWW - YDS$ |
| % Yield Loss (% YL) | $\% YL = ((YWW - YDS)/YWW) \times 100$ |
| % Yield Increase (Well-Watered) (% $YI_{WW}$) | $\% YI_{WW} = (YWW_{TE}/YWW_{CH}) - 1.0) \times 100$ |
| % Yield Increase (Drought Stress) (% $YI_{DS}$) | $\% YI_{DS} = ((YDS_{TE}/YDS_{CH}) - 1.0) \times 100$ |
| Yield Protection (YP; bu/ac) | $YP\ bu/ac = (YWW_{CH} - YDS_{CH})/$ $(YWW_{TE} - YDS_{TE})$ |
| % Yield Protection (% YP) | $\% YP = (YWW_{CH} - YDS_{CH})/$ $(YWW_{TE} - YDS_{TE}) \times 100$ |

TABLE 4

Secondary parameters and measurement method.

| Parameter | Methodology |
| --- | --- |
| Plant Height (in cm) | Physical measurement of uppermost leaf tip with meter stick |
| V-stage | Leaf count from earliest emerging leaf collar designated as V-stage |
| Newest Emerging Leaf V number | Physically count up from the V-stage leaf to the innermost, youngest leaf emerging from the primary whorl. |
| Leaf Surface Temperature (LST) | Sixth Sense Handheld IR Thermometer (LT300) Data logger information was synchronized to the leaf surface temperature measurement to ensure correlation of the results. Prior to measuring leaf temperature, the portable data logger was placed at the center of the whorl and the time of day, Relative Humidity, Air Temperature and Dew Point data were logged. Tests were made on the most fully expanded mature leaf in the uppermost portion of the leaf canopy (typically 2 leaves younger than the V-stage leaf). Non-shaded areas mid way between the midrib and the leaf edge and perpendicular to the lights were chosen for the tests. The handheld device was held about 1-2 inches from the leaf and a path of approximately 2-3 inches along the lamina was scanned (recording in averaging mode). |
| Quantum Yield (QY; light adapted; photosystem II) | FLUORPEN Handheld QY Sensor (Qubit Systems Inc., Kingston, Ontario) Light-adapted (Fv'/Fm'): The same leaf positions and locations on the leaves as were probed for the leaf temperature measurements were tested. The sensor was gently placed on a non shaded region of the leaf and the QY value was recorded. |
| Leaf wilt and roll phenotype | Visual inspection was done at mid-day during the 5 day period of stage 2 drought (typically when signs of subtle wilting began). Each plant was visually inspected and assigned a score ranging from 0 (no sign of stress) to 3 (most severe). |
| Leaf Relative Water Content (RWC) | A 1 inch square leaf lamina sample from the most mature fully expanded leaf was placed into a tared tube with cap 7 days prior to harvest and weighed to obtain fresh weight (FW). The tube was filled with deionized water and placed at 4° C. After 24 hours of soaking, the leaf sample was gently patted dry to remove excess surface water and weighed to obtain the turgid weight (TW). The leaf sample was then air dried (75° C.) for 3 days and weighed to obtain the dry weight (DW). Percent RWC = [(FW − DW)/(TW − DW)] × 100 |
| Leaf Elongation Measurements | The newest emerging leaf was marked gently with a permanent marker. A meter stick was used to measure the distance from the soil level to the leaf tip for 5 consecutive days at the same time each day. For relative leaf elongation calculations, elongation of each individual plant each day was determined relative to the average of the control plants of the respective group. |
| Photosynthesis, Transpiration and Conductance readings | Li-COR ® 6400 portable system (LI-COR Biosciences, Lincoln, NE) Measurements were taken on the same leaf as was probed for the QY and LST measurements. |

Four (ZX1332-430, ZX1332-433, ZX1532-292 and ZX1675-736) of the 8 transgenic events showed significant differences in the TRP, a measure of the relative soil transpirable water at which plants begin to reduce their transpiration rate. Three others (ZX1332-136, ZX1332-168 and ZX1332-660) showed significant reductions in RLST and one of these (ZX1675-660) showed a greater quantum yield of photosynthesis than the non-transgenic controls after negative control plants showed signs of water stress.

FIG. 1 presents the measurements taken for several B104pEPS1004 transgenic lines expressing the ZmRING gene that were grown and tested in the greenhouse. A numerical score was given to the key parameters measured in the screen to produce a Total Selection Score (TSS). The primary measurement (Transpiration Reduction Point; Table 3) was weighted more strongly than the secondary parameters (RLST and QY). Statistical significance was determined by $p<0.05$, $\alpha=0.05$ ($\alpha=0.10$, for trends). A finding of no statistical difference was given a score of zero. For a particular construct tested, at least two lines were required to have a TSS score of 1 or above to be designated as "PASS" (FIG. 1). It is noted that plants for 4 lines tested had a TSS score of 1 or above. In particular, 4 maize transgenics produced by transformation with plasmid pEPS1004, which harbors a ZmRING coding region under control of a maize ubiquitin1 promoter, and designated as lines ZX1332-430, ZX1332-433, ZX1532-292 and ZX1675-736, had a TSS score of 1 or above. Thus the pEPS1004 plants expressing ZmRING were found to be as drought tolerant as plants of the positive control nontransgenic (drought tolerant) line DASDT69. Measured values for the 10 lines summarized in FIG. 1 are presented in Table 5.

TABLE 5

Greenhouse plant test results for 10 maize pEPS1004-transformed transgenic lines expressing the ZmRING protein. Values obtained by the methods in Table 3 and Table 4. For RLST and QY, data shown are for most significant measurement day of those taken over several days.

| | | TRP | | | | | | RSLT | | | QY | | |
|---|---|---|---|---|---|---|---|---|---|---|---|---|---|
| Expt | Line | Mean | StdEr | N | CL+ | CL− | Significant? | Mean | Stdev | p-value | Mean | Stdev | p-value |
| 1 | B104 | −0.301 | 0.006 | 10 | −0.29 | −0.313 | no | 1.02 | 0.04 | 1 | 0.64 | 0.06 | 1 |
| 1 | DASDT69 | −0.261 | 0.007 | 12 | −0.25 | −0.275 | yes | 0.99 | 0.04 | 0.07 | 0.69 | 0.05 | 0.45 |
| 1 | ZX1332-136 | −0.31 | 0.009 | 8 | −0.29 | −0.326 | no | 0.97 | 0.03 | 0.01 | 0.67 | 0.07 | 0.91 |
| 1 | ZX1332-1414 | −0.304 | 0.009 | 5 | −0.29 | −0.321 | no | 1.03 | 0.05 | 0.98 | 0.65 | 0.04 | 1 |
| 1 | ZX1332-430 | −0.237 | 0.012 | 3 | −0.21 | −0.261 | yes | 1.02 | 0.02 | 1 | 0.58 | 0.09 | 0.52 |
| 1 | ZX1332-433 | −0.189 | 0.014 | 4 | −0.16 | −0.217 | yes | 1.01 | 0.03 | 1 | 0.68 | 0.03 | 0.91 |
| 2 | B104 | −0.38 | 0.012 | 14 | −0.36 | −0.403 | no | 1.08 | 0.03 | 1 | 0.45 | 0.08 | 1 |
| 2 | DASDT69 | −0.283 | 0.014 | 9 | −0.26 | −0.311 | yes | 1.03 | 0.02 | 0 | 0.64 | 0.09 | 0 |
| 2 | ZX1532-168 | −0.388 | 0.011 | 11 | −0.37 | −0.41 | no | 1.01 | 0.03 | <.0001 | 0.5 | 0.11 | 0.6 |
| 2 | ZX1532-292 | −0.279 | 0.013 | 11 | −0.25 | −0.304 | yes | 1.03 | 0.04 | 0 | 0.58 | 0.07 | 0.01 |
| 2 | ZX1532-391 | −0.434 | 0.013 | 11 | −0.41 | −0.46 | no | 1.1 | 0.04 | 0.26 | 0.52 | 0.13 | 0.3 |
| 3 | B104 | −0.361 | 0.014 | 11 | −0.33 | −0.389 | no | 1.13 | 0.04 | 1 | 0.51 | 0.11 | 1 |
| 3 | DASDT69 | −0.309 | 0.013 | 12 | −0.28 | −0.334 | yes | 1.06 | 0.03 | <.0001 | 0.65 | 0.08 | 0.02 |
| 3 | ZX1675-660 | −0.318 | 0.012 | 12 | −0.3 | −0.341 | no | 1.06 | 0.02 | <.0001 | 0.65 | 0.04 | 0.02 |
| 3 | ZX1675-733 | −0.34 | 0.014 | 12 | −0.31 | −0.367 | no | 1.12 | 0.03 | 0.9 | 0.51 | 0.17 | 1 |
| 3 | ZX1675-736 | −0.305 | 0.01 | 12 | −0.29 | −0.324 | yes | 1.14 | 0.03 | 0.7 | 0.41 | 0.15 | 0.19 |

Therefore, it was found that production of a ZmRING protein in transgenic plants grown under drought conditions in the greenhouse provides a boost in drought protection to maize plants having a normally drought susceptible genetic background.

EXAMPLE 6

Field Testing of EPS1004 Transgenic Maize Plants in Chile (2009-2010)

Drought Tolerant Genetic Background

Progeny plants derived from transgenic B104 plants that expressed the plant-optimized ZmRING gene (Example 4) were tested in field conditions in Chile to determine yield advantage of the transgenic plants compared to nontransgenic isolines under drought conditions. A transgenic plant (T0) was crossed with parent B104 to create first generation seeds (T1). The T1 seeds were then planted and self-pollinated at a nursery field in Hawaii. After molecular analysis to identify single copy homozygous plants, events meeting these criteria were self-pollinated to create 2nd generation seeds (T2). The homozygous T1 plants were also used to cross with elite Dow AgroSciences inbred testers (a drought tolerant line, DASDT69) and a drought susceptible line (6XN442) to create F1 hybrids. Plants grown from second generation homozygous seeds (T2) and 2nd generation F1 hybrid seeds were tested in the field.

Field experiments were conducted at Tuniche experimental station (latitude 34° 10' 0" S, and longitude 70° 45' 0" W) from October 2009 to May 2010. Hybrid lines derived from transgenic plants containing the ZmRING gene were tested. Plants from event 0643 were crossed to the drought-tolerant DASDT69 background to generate Hybrid Line 1 and Hybrid Line 2. Plants from B104 events 0643, 0430 and 0168 were crossed to the drought-susceptible 6XN442 background to generate Hybrid Line 3, Hybrid Line 4, Hybrid Line 5 and Hybrid Line 6. Non-transgenic Checks consisting of plants of F1 hybrids DASDT69/B104 and 6XN442/B104 were also grown.

The experiment was designed as split-plot with water treatment as the main factor and transgenic entries as a sub-factor. Plant entries were arranged in the replicated plots according to a randomized complete block design. Well-watered treatments had 3 to 5 replications and drought treatments had 6 or 7 replications. Each plot was 17.5 feet long, containing two rows (30 inch row spacing) with 6 inches plant spacing. Seeds (40 kernels) were planted using a cone seeder in each plot. Local recommended management practices were employed to achieve maximum yield.

Two irrigation treatments were imposed, with water supplied by drip irrigation. For the well-watered treatment, water was supplied throughout the growing period to obtain maximum yield. (The term "well-watered" in this context refers to the amount of water applied, and not the source of the water supply). Evapotranspiration values (Allen et al., 1998, FAO Irrigation and Drainage Paper No. 56. FAO, Rome, Italy) were computed for each location based on local weather conditions. Well-watered treatments received 100% of corn evapotranspiration water demand throughout the growing period. Drought treatments received 100% of corn evapotranspiration water during most of the corn growing period, except for a 4 to 5 week period beginning at about the V11 corn growth stage (approximately 14 days before pollination (V12 stage) to 14 days after pollination). During the drought period, water was withheld from the drought treatments for the first two weeks, resulting in depletion of reserve soil moisture. Then, a fraction (about 60%) of evapotranspiration water demand was provided to the drought stress treatments for the duration of 3 weeks. Typically, peak corn pollination occurred during this three week period, therefore the moisture stress period was scheduled so that the moisture stress level was at the peak during the pollination period. Normal watering was then resumed. The target intensity of drought stress was 20-50% yield reduction in drought treatments as compared to optimum irrigation. All other management practices, including fertilizer application, weed control, insect and disease control, followed local practices and were universally applied for all test groups.

For each two-row plot, both rows were hand harvested for yield determination. Total kernel numbers for the 5 ears from each harvested row were recorded. Plot yield was adjusted at a moisture content of 15%.

For all experimental data, statistical analyses were completed using JMP software (Version 9.0., SAS Institute Inc., Cary, N.C.). All data were subjected to analysis of variance (ANOVA). If significant differences were found (P<0.05), comparisons with controls were performed using student test at P<0.05.

Yield of Zmring Transgenic Hybrids Having a Drought Tolerant Background

Yields of two ZmRING transgenic hybrids with the drought-tolerant DASDT69 background are summarized in Table 6.

Under well-watered conditions, there were no statistically significant yield differences between the tested hybrid lines and yield of the Check. No yield drag or detrimental agronomic effects were observed during the growing period for phenotypic, physiological and agronomic traits. Thus, these results indicated that there are no undesired effects of the ZmRING gene on agronomic performance, and under well-watered conditions, both hybrid lines performed well.

Under drought stress conditions Hybrid line 1 (DASDT69/B104pEPS1004-0643-003.001) had the highest yield of 92 bu/ac (Table 6). Both Hybrid Line 1 and Hybrid Line 2 had greater yields than the non-transgenic line Check 1 (DASDT69/B104). High yield was mainly attributed to an increase in kernel numbers of the ear but not to the kernel weight per ear (Table 6).

Yield Increase was calculated by the formula in Table 3. Under drought stress conditions, Hybrid Line 1 had a yield increase of 35% and Hybrid Line 2 had a yield increase of 14%.

Yield Protection was calculated by the formula in Table 3. Yield Protection is a reflection of the performance of transgenic events under well watered and drought stress conditions and therefore serves as an indicator of any yield drag and detrimental effects of the transgene under optimum condition, as well as the yield increase under drought conditions. Hybrid Line 1 and Hybrid Line 2 had yield protection values of 12% and 5%, respectively, compared to the Check (Table 6). It is therefore a finding of this invention that production of the ZmRING protein in transgenic plants under drought conditions in the field provides a boost in drought protection to maize plants having a normally drought tolerant genetic background.

Drought Susceptible Genetic Background

Four hybrid transgenic progeny lines derived from crosses of ZmRING B104 transgenic plants (Example 4) crossed with the drought susceptible 6XN442 genetic background were tested in field conditions under the same conditions as described above for transgenics crossed with the drought tolerant DASDT69 background. Yields of the transgenic hybrids in the drought susceptible background are given in Table 7.

TABLE 6

Yield and yield components of two DASDT69/B104pEPS1004 hybrid lines tested under well-watered and drought conditions in field plots in Chile. Both lines are ZmRING transgenic hybrids with a drought tolerant DASDT69 background. Hybrid Line 1 was DASDT69/B104pEPS1004-0643-003.001, and Hybrid Line 2 was DASDT/B104pEPS1004-0643-003.002.

| Condition | Name | Event | Yield bu/ac (SD*) | Kernel No./ear | Total Kernel Wt (gm) | % Yield Increase*** | Yield Protection (bu/ac)*** | % Yield Protection*** |
|---|---|---|---|---|---|---|---|---|
| Well-watered | Hybrid Line 1 | 0643 | 196 (23) | ND* | ND | 0 | NA* | NA |
| | Hybrid Line 2 | 0643 | 193 (12) | ND | ND | 0 | NA | NA |
| | Check 1** | | 193 (21) | ND | ND | 0 | NA | NA |
| Drought | Hybrid Line 1 | 0643 | 92 (30) | 235 | 0.43 | 35 | 21 | 12 |
| | Hybrid Line 2 | 0643 | 78 (28) | 189 | 0.47 | 14 | 10 | 5 |
| | Check 1** | | 68 (22) | 181 | 0.56 | 0 | NA | NA |

*Abbreviations: SD = Standard Deviation; ND = Not Done; NA = Not Applicable
**Check 1 are plants of an isogenic F1 hybrid: DASDT69/B104.
***See text and Table 3 for calculation.

TABLE 7

Yield and yield component of four 6XN442/B104pEPS1004 hybrid lines tested under well-watered and drought conditions in field plots in Chile. All events are ZmRING transgenic hybrids with the drought susceptible 6XN442 background. Hybrid Line 3 is 6XN442/B104pEPS1004-0643-003.001; Hybrid Line 4 is 6XN442/B104pEPS1004-0643-003.002; Hybrid Line 5 is 6XN442/B104pEPS1004-0430-002.001; and Hybrid Line 6 is 6XN442/B104pEPS1004-0168-002.002.

| Condition | Name (N)* | Event | Yield bu/ac SD* | Kernel No./ear | Average Kernel Wt (gm) | % Yield Increase*** | Yield Protection (bu/ac)*** | % Yield Protection*** |
|---|---|---|---|---|---|---|---|---|
| Well-Watered | Hybrid Line 3 (5) | 0643 | 201 (17) | ND* | ND | 0 | NA* | NA |
| | Hybrid Line 4 (5) | 0643 | 201 (15) | ND | ND | 0 | NA | NA |
| | Hybrid Line 5 (5) | 0430 | 208 (11) | ND | ND | 0 | NA | NA |
| | Hybrid Line 6 (5) | 0168 | 199 (20) | ND | ND | 0 | NA | NA |
| | Check 2** (12) | | 208 (12) | ND | ND | 0 | NA | NA |
| Drought | Hybrid Line 3 (7) | 0643 | 82 (29) | 202 | 0.605 | 3 | 9 | 2 |
| | Hybrid Line 4 (7) | 0643 | 84 (24) | 310 | 0.329 | 5 | 11 | 3 |
| | Hybrid Line 5 (7) | 0430 | 84 (28) | 215 | 0.335 | 5 | 3 | 2 |
| | Hybrid Line 6 (7) | 0168 | 79 (32) | 245 | 0.346 | −1 | 8 | 1 |
| | Check 2** (21) | | 80 (24) | 244 | 0.401 | 0 | NA | NA |

*Abbreviations: N = Number of replicates; SD = Standard Deviation; ND = Not Done; NA = Not Applicable
**Check 2 are plants of an isogenic F1 hybrid: 6XN442/B104.
***See text and Table 3 for calculation.

Under well watered conditions, there were no statistically significant yield differences between the tested hybrid lines and Check 2 (an isogenic F1 hybrid: 6XN442/B104). No yield drag or detrimental agronomic effects were observed during the growing period for phenotypic, physiological and agronomic traits. Thus, these results indicated that there are no undesired effects of the ZmRING gene on agronomic performance, and under well-watered conditions, all events performed well.

Under drought conditions, transgenic hybrids containing a ZmRING coding region showed an increase in grain yield relative to the untransformed control.

EXAMPLE 7

Field Testing in Chile 2011-2012

Field experiments were conducted at Tuniche experimental station (latitude 34° 10' 0" S, and longitude 70° 45' 0" W) from October 2011 to May 2012. Hybrid lines derived from transgenic plants containing the ZmRING gene were tested. Plants from B104 events 0643, 0430 and 0168 were crossed to the drought-susceptible 6XN442 background to generate Hybrid Line 1, Non-transgenic Checks consisting of plants of F1 hybrids 6XN442/B104 were also grown.

Two-row, 17.5-ft plots were established for primary screening under an acute period of drought stress applied prior to and including flowering. Trials were established as an unbalanced split plot, randomized complete block design with 6-9 replications of a mild water-stressed treatment main block (consisting of 30-60% replacement of predicted evapotranspiration needs, $ET_c$), a severe water-stressed treatment main block with 6-9 replications (consisting of 10-30% replacement of predicted, $ET_c$) and compared to well-watered plots (3 replicates) that received 100% $ET_c$ replacement. Trials were established at two populations in an additional split plot consisting of 34,000 and 44,000 plants per hectare. Trials were established by providing the crop's full predicted water needs until the V8-V11 growth stage. Water was then withheld for a period of 7-21 days (until the first signs of drought stress were observed). Mild stress was then accomplished by replacing 30-60% of $ET_c$ for 21 days (approximate growth stage V14 through R3). The remainder of the season plants received 100% predicted $ET_c$ replacement. Severe stress was accomplished by replacing 10% of $ET_c$ for 21 days (approximate growth stage V14 through R3). The remainder of the season plants received 100% predicted $ET_c$ replacement. Yield is reported as average ton/Ha at 15.5% moisture.

TABLE 8

Yield and yield component of one 6XN442/B104pEPS1004 hybrid line tested under well-watered, mild and severe-drought conditions in field plots in Chile. The 6XN442/B104_pEPS1004_ZX1675-736_Hybrid-1 line contains the ZmRING transgene in the B104 background and is a hybrid with the drought susceptible line 6XN442. Yield is expressed as a percentage of the non-trangenic control line 6XN442/B104.

| Name | Yield (ton/Ha at 15.5% moisture) | | | Percent Yield Increase | | |
|---|---|---|---|---|---|---|
| | High Stress | Mild Stress | Well watered | High Stress | Mild Stress | Well watered |
| 6XN442/B104_pEPS1004_ZX1675-736_Hybrid-1 | 8.22 | 10.09 | 14.2 | 22% | 13% | −12% |
| 6XN442/B104 | 6.75 | 8.95 | 16.21 | 0% | 0% | 0% |

EXAMPLE 8

Field Testing in Texas and California

Progeny plants derived from transgenic B104 plants that expressed the plant-optimized ZmRING gene (Example 4) were tested in field conditions in Texas and California. A transgenic plant (T0) was crossed with parent B104 to create first generations seeds (T1). The T1 seeds were then planted and self-pollinated at a nursery field in Hawaii. After molecular analysis, single copy, homozygous events were self-pollinated to create 2nd generation lines (T2). These plants were further self pollinated for two more generations to generate T4 inbred lines. The T2 homozygous plants were also used to cross with elite Dow AgroSciences inbred drought susceptible line (6XN442) to create F1 hybrids. Plants grown from T4 inbred and hybrid seeds were tested in the field at one site in Texas and two sites in California.

The experiments were designed essentially as described in Example 6. Well-watered treatments received sufficient irrigation to supply 100% of evapotranspiration water demand throughout the growing period. Drought treatments received 100% of evapotranspiration water during most of the corn growing period, except for a 4 to 5 week period beginning at about the V11 corn growth stage (approximately 14 days before pollination (V12 stage) to 14 days after pollination). During the drought period, water was withheld from the drought treatments for the first two weeks, resulting in depletion of reserve soil moisture. Then, a fraction (about 60%) of evapotranspiration water demand was provided to the drought stress treatments for the duration of 3 weeks. At the Texas site, the well-watered hybrid plants received 34.5 inches of water over the entire growing season, with 18.8 inches being applied during the drought stress period. The drought-stressed hybrid plants received 26.1 inches total water for the growing season and only 10.5 inches of water during the stress period. The well-watered inbred plant plots received 70% to 75% of the total water applied to the hybrid plant plots, following the watering regime as described above.

At the California sites, to obtain optimum corn growth, well-watered plots received sufficient water to restore 100% of the evapotranspiration loss. Well-watered inbred plots received a seasonal total of 19.5 inches of water, with 12.9 inches of this water provided during drought stress period. Drought-stressed inbred plots received a seasonal total of 8.34 inches of water with 1.74 inches of water provided during the 4-week drought stress period. All other management practices, including fertilizer application, weed control, insect control, and disease control, followed local practices and were universally applied for all test groups.

Grain yields and other plant growth measurements were collected and calculated as disclosed in the previous Examples.

Hybrid plant tests in Texas

Table 9 presents the yield results of plants of transgenic and check hybrid lines obtained in the Texas field plot. Plants from eleven of the twelve hybrid lines tested had a higher yield than the Check plants, with the Yield Increase ranging from 1% to 14%. The 14% Yield Increase of Entry 29 (Hybrid Line 6XN442/B104pEPS1004-0168) was significant by the t-test (p=0.05). Three hybrid lines (Entries 29, 30 and 18) had the highest value of 9% Yield Protection under drought conditions. It is to be noted that plants from Entry 29 (Hybrid Line 6XN442/B104pEPS1004-0168), were also tested in Chile (Table 7, Hybrid Line 6) where a % Yield Protection of 1% was seen. Further, plants from Entry 18 (Hybrid Line 6XN442/B104pEPS1004-0643) were tested in Chile (Table 7, Hybrid Lines 3 and 4) where they gave a % Yield Protection of 2% and 3%, respectively.

TABLE 9

Yield analyses of plants of 15 6XN442/B104pEPS1004 hybrid lines tested under well-watered and drought conditions in field plots in Texas. All Entries are ZmRING transgenic hybrids with the drought susceptible 6XN442 background.

| Entry No. | Event | Mean bu/ac* | Std Err Mean | % Yield Increase | % Yield Protection |
|---|---|---|---|---|---|
| 29 | 0168 | 132 | 7 | 14 | 9 |
| 30 | 303 | 129 | 5 | 12 | 9 |
| 18 | 0643 | 127 | 10 | 11 | 9 |
| 26 | 433 | 125 | 11 | 8 | 2 |
| 27 | 428 | 123 | 7 | 6 | 7 |
| 24 | 292 | 121 | 7 | 5 | 1 |
| 17 | 1061 | 120 | 9 | 4 | 7 |
| 16 | 325 | 120 | 8 | 4 | 2 |
| 20 | 647 | 118 | 8 | 2 | 0 |
| 21 | 899 | 117 | 6 | 1 | −1 |
| 23 | 702 | 117 | 5 | 1 | 3 |
| 47 | Control | 115 | 7 | 0 | 0 |
| 28 | 136 | 115 | 8 | 0 | 2 |

*Yield under drought-stressed conditions

Inbred Plant Tests in Texas

Table 10 presents results of plants of transgenic inbred events obtained in the Texas field plot, compared to the B104 inbred Check plants. Plants from 5 of the 15 inbred lines tested had a higher yield than the Check plants, with the Yield Increase ranging from 1% to 14%. Of the entries that had increased yield, one entry (Entry 16) had a Yield Protection value of 7% under drought conditions.

TABLE 10

Yield analyses of plants of 15 B104pEPS1004 inbred lines tested under well-watered and drought conditions in field plots in Texas. All events are ZmRING transgenic inbreds with the drought susceptible B104 background.

| Entry No. | Event | Mean bu/ac* | Std Err Mean | % Yield Increase | % Yield Protection |
|---|---|---|---|---|---|
| 19 | 1022 | 85 | 11 | 14 | 3 |
| 16 | 325 | 81 | 8 | 8 | 7 |
| 18 | 643 | 79 | 6 | 5 | -4 |
| 26 | 433 | 77 | 16 | 3 | 1 |
| 29 | 168 | 75 | 7 | 1 | -10 |
| CK | Control | 75 | 9 | 0 | 0 |
| 22 | 187 | 73 | 11 | -2 | -8 |
| 17 | 1061 | 73 | 8 | -3 | 16 |
| 20 | 647 | 71 | 18 | -4 | -6 |
| 28 | 136 | 71 | 6 | -5 | -7 |
| 24 | 292 | 70 | 16 | -6 | -6 |
| 27 | 428 | 66 | 12 | -11 | 3 |
| 25 | 267 | 66 | 14 | -11 | -8 |
| 30 | 303 | 63 | 8 | -15 | -7 |
| 21 | 899 | 51 | 10 | -32 | -19 |
| 23 | 702 | 39 | 12 | -48 | -25 |

*Yield under drought-stressed conditions

TABLE 11

Yield analyses of plants of 15 B104pEPS1004 inbred lines tested under well-watered and drought conditions in field plots in California. All events are ZmRING transgenic inbred lines with the drought susceptible B104 background, and all were also tested in Texas.

| Entry No. | Event | N | Mean bu/ac* | Std Err Mean | % Yield Increase | % Yield Protection |
|---|---|---|---|---|---|---|
| 30 | 303 | 11 | 78.1 | 18.3 | 27 | 23 |
| 18 | 643 | 12 | 72.1 | 16 | 17 | 6 |
| 24 | 292 | 11 | 71.9 | 11.6 | 17 | 38 |
| 27 | 428 | 11 | 64.9 | 17.1 | 6 | 7 |
| 28 | 136 | 11 | 63.5 | 12.2 | 3 | 12 |
| 23 | 702 | 12 | 61.8 | 11.4 | 1 | 9 |
| CK | Control | 12 | 61.5 | 2.6 | 0 | 0 |
| 25 | 267 | 9 | 55.2 | 21 | -10 | 3 |
| 29 | 168 | 11 | 54.4 | 6.2 | -12 | -3 |
| 16 | 325 | 10 | 52.9 | 13.8 | -14 | -2 |
| 21 | 899 | 11 | 52.2 | 12.9 | -15 | 3 |
| 20 | 647 | 11 | 50 | 9.9 | -19 | -3 |
| 22 | 187 | 12 | 49.8 | 11.4 | -19 | 8 |
| 19 | 1022 | 12 | 45.9 | 5 | -25 | -10 |
| 26 | 433 | 11 | 38.1 | 7.4 | -38 | 9 |
| 17 | 1061 | 11 | 31.6 | 5.2 | -49 | -16 |

*Number of replicates
**Yield under drought-stressed conditions

Severe weather destroyed the hybrid test plots in California.

Inbred Plant Test Results in California

Table 11 presents California field plot results obtained with plants of the same 15 transgenic inbred lines as were tested in Texas, compared to the B104 inbred Check plants. Plants from 6 of the 15 events tested had a higher yield than the Check plants, with the Yield Increase ranging from 1% to 27%. One entry (Entry 30) had the highest value of 23% Yield Protection under drought conditions.

When measured, selected secondary physiological parameters (e.g. ASI, leaf rolling and severity, etc.; Table 4) were statistically correlated with yields across all lines at both test sites.

Table 12 summarizes the results of the hybrid lines and inbred lines obtained in field plot tests in the Texas and California locations.

TABLE 12

Summary of field trial results obtained at Texas and California locations.

| | | Texas | | | | California | |
| | | Female Crossing Parent | | | | | |
| | | 6XN442 | | B104 | | B104 | |
| | | Genetic Class | | | | | |
| | | Hybrid | | Inbred | | Inbred | |
| Entry No. | B104 Transgenic Event (Male Crossing Parent) | % Yield Increase | % Yield Protection | % Yield Increase | % Yield Protection | % Yield Increase | % Yield Protection |
|---|---|---|---|---|---|---|---|
| 16 | B104{pEPS1004-325}.012 | 4 | 2 | 8 | 7 | -14 | -2 |
| 17 | B104{pEPS1004-1061}.003 | 4 | 7 | -3 | 16 | -49 | -16 |
| 18 | B104pEPS1004-0643* | 11 | 9 | 5 | -4 | 17 | 6 |
| 19 | B104{pEPS1004-1022}.010 | -3 | 0 | 14 | 3 | -25 | -10 |
| 20 | B104{pEPS1004-647}.006 | 2 | 0 | -4 | -6 | -19 | -3 |
| 21 | B104{pEPS1004-899}.009 | 1 | -1 | -32 | -19 | -15 | 3 |
| 22 | B104{pEPS1004-187}.006 | -6 | -2 | -2 | -8 | -19 | 8 |
| 23 | B104{pEPS1004-702}.008 | 1 | 3 | -48 | -25 | 1 | 9 |
| 24 | B104{pEPS1004-292}.012 | 5 | 1 | -6 | -6 | 17 | 38 |
| 25 | B104{pEPS1004-267}.005 | -2 | -2 | -11 | -8 | -10 | 3 |
| 26 | B104/pEPS1004-433.004 | 8 | 2 | 3 | 1 | -38 | 9 |
| 27 | B104{pEPS1004-428}.005 | 6 | 7 | -11 | 3 | 6 | 7 |
| 28 | B104pEPS1004-0136 | 0 | 2 | -5 | -7 | 3 | 12 |
| 29 | B104pEPS1004-0168** | 14 | 9 | 1 | -10 | -12 | -3 |
| 30 | B104{pEPS1004-303}.004 | 12 | 9 | -15 | -7 | 27 | 23 |
| 47 | 6XN442/B104 (Check) | 0 | 0 | NA | NA | NA | NA |
| CK | B104 (Check) | NA | NA | 0 | 0 | 0 | 0 |

*Plants from crosses of this event with DASDT69 (Table 6) and 6XN442 (Table 7; Hybrid Lines 3 & 4) were tested in field plots in Chile.
**Plants from crosses of this event with 6XN442 were tested in field plots in Chile (Table 7; Hybrid Line 6).

Thus, expression of the ZmRING gene to produce the ZmRING protein in the drought-susceptible B104/6XN442 genetic hybrid background provides protection from drought stress, as particularly exemplified by Entry 18 (B104pEPS1004-0643), Entry 29 (B104pEPS1004-0168) and Entry 30 (B104{pEPS1004-303}.004).

EXAMPLE 9

ZmRING-Homologous Sequences from Drought Tolerant Maize Hybrids and Inbreds

In some exemplifications of the methods of this disclosure, it is desirable to employ a ZmRING-homologous gene derived from a maize line such as a drought-tolerant inbred or hybrid maize line. Such a gene, including the protein coding region and associated expression regulatory elements, may be identified and isolated by means of several different methods well known to those skilled in the field of plant molecular biology, including the genome walking method. Substantial guidance for the isolation of genomic fragments and sequences is available, for example, as published by Leoni et al. (2011, FEBS J. August 17 issue). Exemplary but non-limiting examples of ZmRING-homologous genes are obtained using materials such as leaf tissues from selected maize lines, for example, from a drought-tolerant maize inbred line such as 7SH382, BS112, SLMO3 and WDC69, among others, and from a drought-tolerant hybrid line such as hybrid 2A120, among others. These tissues are used for genomic DNA isolation using a DNeasy PLANT MAXI KIT™ (QIAGEN; Valencia, Calif.). Genomic DNA libraries are constructed by the use of a GENOMEWALKER™ kit (CLONTECH LABORATORIES, INC; Mountain View, Calif.). Isolation of ZmRING-homologous genomic DNA is accomplished by PCR amplification using high fidelity DNA polymerase, adaptor-specific primers, and gene-specific primers designed from a B73 ZmRING sequence (SEQ ID NO:1). The resulting PCR amplified products are cloned into appropriate plasmid vectors and the DNA sequences of the inserts are determined. Consensus sequences of the genomic clones are compiled from the sequences of the products of multiple independent PCR reactions. In this manner, DNA polymerase-generated sequence errors, introduced during the multiple cycles of PCR amplification necessary to obtain the genomic fragment amplicons, may be identified and eliminated. Using standard sequence alignment algorithms, an assembled genomic sequence from each maize line is aligned to the sequence of a B73 ZmRING gene (SEQ ID NO: 1) to determine the location(s) of ZmRING-homologous coding regions(s) and associated expression regulatory sequence elements.

What is claimed is:

1. A transgenic monocotyledous plant comprising in its genome a stably-integrated, recombinant DNA construct comprising a polynucleotide operably linked to at least one regulatory element, wherein said polynucleotide has a nucleic acid sequence encoding SEQ ID NO: 2, and wherein said monocotyledous plant exhibits increased drought tolerance when compared to a control plant not comprising said recombinant DNA construct.

2. The transgenic monocotyledous plant of claim 1, wherein the polynucleotide comprises SEQ ID NO: 1 or SEQ ID NO: 3.

3. The transgenic monocotyledous plant of claim 1, wherein the plant is a maize plant, wheat plant or rice plant.

4. The transgenic monocotyledous plant of claim 2, wherein the plant is a maize plant, wheat ant or rice plant.

5. The transgenic monocotyledons plant of claim 1, wherein said plant has an increased yield when grown under drought stress as compared to a non-transformed control plant of the seine species.

6. The transgenic monocotyledous plant of claim 1, wherein the plant further comprises at least one additional agronomic trait, herbicide trait or insecticide trait.

7. A method of increasing drought and/or heat tolerance in a monocotyledous plant, comprising: (a) introducing into a regenerable plant cell a recombinant DNA construct comprising a polynucleotide operably linked to at least one regulatory sequence, wherein the polynucleotide has a nucleic acid sequence encoding SEQ ID NO: 2; and (b) regenerating a transgenic plant from the regenerable plant cell after step (a), wherein the transgenic plant comprises stably-integrated in its genome the recombinant DNA construct and the transgenic plant exhibits increased drought tolerance when compared to a control plant not comprising the recombinant DNA construct.

8. The method according to claim 7, further comprising: (c) obtaining a progeny plant derived from the transgenic plant, wherein said progeny plant comprises stably-integrated in its genome the recombinant DNA construct and exhibits increased drought tolerance when compared to a control plant not comprising the recombinant DNA construct.

9. The method according to claim 7, wherein the polynucleotide comprises SEQ ID NO: 1 or SEQ ID NO: 3.

10. The method according to claim 7, wherein the plant further comprises at least one additional agronomic trait, herbicide trait or insecticide trait.

11. A method of improving drought tolerance in a corn line comprising crossing a corn plant of said corn line with a drought tolerant transgenic corn plant having a recombinant DNA expressing a protein having the amino acid sequence of SEQ ID NO:2 to produce a corn seed having the recombinant DNA.

12. A method for increasing yield in a corn crop subject to water deficit during its growth, said method comprising planting transgenic seeds having a stably-integrated, recombinant DNA, wherein the stably-integrated, recombinant DNA comprises the nucleic amino acid sequence of SEQ ID NO:1 or SEQ ID NO: 3 or wherein the stably-integrated, recombinant DNA encodes a protein having the amino acid sequence of SEQ ID NO:2 and allowing said seeds to grow to mature corn plants while being subjected to drought during at least one ten day period during vegetative phase of growth.

13. A drought tolerant transgenic corn plant having a recombinant DNA expressing a protein having the amino acid sequence of SEQ ID NO:2.

14. The transgenic corn plant of claim 13, wherein said corn plant further comprises at least one additional agronomic trait, herbicide trait or insecticide trait.

15. Transgenic seed for growing a drought tolerant corn plant, said seed comprising in its genome a stably-integrated, recombinant DNA encoding a protein having the amino acid sequence of SEQ ID NO: 2.

16. A DNA construct comprising a nucleic acid encoding the polypeptide of SEQ ID NO: 2, wherein the nucleic acid is operably linked to a heterologous regulatory element and wherein SEQ ID NO: 2 increases the maintenance of membrane integrity under abiotic stress in a plant cell.

17. The DNA construct of claim 16, wherein the nucleic acid has been optimized for expression in a plant.

18. The DNA construct of claim 16, wherein the nucleic acid comprises the nucleotide sequence of SEQ ID NO: 3.

19. A plant expression vector comprising the DNA construct of claim 16.

20. A transgenic plant cell comprising, stably-integrated in its genome, the DNA construct of claim 16.

21. A transgenic plant cell culture, plant tissue, or whole plant comprising the transgenic plant cell of claim 20.

22. A method for making a transgenic monocotyledous plant having an drought related trait relative to a control plant, comprising introducing a recombinant construct into a plant cell, plant, or part thereof, wherein the drought related trait is one or more of: (i) increased early vigor; (ii) increased biomass; (iii) increased total seed yield per plant; (iv) increased seed filling rate; (v) increased harvest index; (vi) increased thousand kernel weight, (vii) increased abiotic stress resistance, or (viii) increased nutrient uptake efficiency, and wherein the construct comprises (a) a nucleic acid sequence encoding the polypeptide of SEQ ID NO: 2; (b) one or more control sequences capable of driving expression of the nucleic acid sequence of (a) and optionally (c) a transcription termination sequence.

* * * * *

SEQUENCE LISTING

```
<160> NUMBER OF SEQ ID NOS: 5

<210> SEQ ID NO 1
<211> LENGTH: 1095
<212> TYPE: DNA
<213> ORGANISM: Zea mays
<220> FEATURE:
<221> NAME/KEY: CDS
<222> LOCATION: (1)..(1092)
<223> OTHER INFORMATION: ZMRING protein

<400> SEQUENCE: 1 atg gag acg gcc acc acg tcg ccg gag cac ccg ctg ctc cgc cgc tca      48
Met Glu Thr Ala Thr Thr Ser Pro Glu His Pro Leu Leu Arg Arg Ser
1               5                   10                  15 tca ccg tcg tcc aat acc aac gcc gac gct gat tct gtc aac ctg tct      96
Ser Pro Ser Ser Asn Thr Asn Ala Asp Ala Asp Ser Val Asn Leu Ser
                20                  25                  30 tcg cct cct ccc tcc gcg gcg agg cca agc cgt ctc gcg gca ctc atc     144
Ser Pro Pro Pro Ser Ala Ala Arg Pro Ser Arg Leu Ala Ala Leu Ile
            35                  40                  45 ggg cgc gtg ggg tgg ccg cgc ggg ccc tcg atg atg gtg cac gag gcg     192
Gly Arg Val Gly Trp Pro Arg Gly Pro Ser Met Met Val His Glu Ala
    50                  55                  60 acg acg ctg cag ctg cat cga agg cgc gcg gac tgg gcg cac tcc cgc     240
Thr Thr Leu Gln Leu His Arg Arg Arg Ala Asp Trp Ala His Ser Arg
65                  70                  75                  80 ccc gtc gtc acg ctc gac atc gcc tgg aac gtc gcc tgc gcc gcc gct     288
Pro Val Val Thr Leu Asp Ile Ala Trp Asn Val Ala Cys Ala Ala Ala
                85                  90                  95 gcg gcc ttg gtg ctc gcg tcc tcc gcc aag gac agc ccc gtg aag cca     336
Ala Ala Leu Val Leu Ala Ser Ser Ala Lys Asp Ser Pro Val Lys Pro
            100                 105                 110 ctc cgc ctg tgg ctc gtc ggg tac gcc gcc cag tgc ctg gtg cac gtc     384
Leu Arg Leu Trp Leu Val Gly Tyr Ala Ala Gln Cys Leu Val His Val
        115                 120                 125 ggg atc gtc ttt acc cgt tcg aga cgc ggg acg cgg cac gcc tgg ggc     432
Gly Ile Val Phe Thr Arg Ser Arg Arg Gly Thr Arg His Ala Trp Gly
```

```
                    130                 135                 140
ccg gcc tca gac gtt gaa tct gcc ggc gca ggg acg gac agc tcg gga    480
Pro Ala Ser Asp Val Glu Ser Ala Gly Ala Gly Thr Asp Ser Ser Gly
145                 150                 155                 160 acc gac agc gaa gat gac gaa acg gcg gaa ggg agg agc agc cat gca    528
Thr Asp Ser Glu Asp Asp Glu Thr Ala Glu Gly Arg Ser Ser His Ala
                165                 170                 175 agt cgt tgt gag acg ata aac agg ttg ata tca ttt ctg tgg tgg atc    576
Ser Arg Cys Glu Thr Ile Asn Arg Leu Ile Ser Phe Leu Trp Trp Ile
            180                 185                 190 att gga ttc tac tgg cta gta tca ggt ggg gag gtg ctg gag tat ggc    624
Ile Gly Phe Tyr Trp Leu Val Ser Gly Gly Glu Val Leu Glu Tyr Gly
        195                 200                 205 gcg cca agg ctt tat tgg tta acc att gtg ttt ctg gcc ttt gat gtg    672
Ala Pro Arg Leu Tyr Trp Leu Thr Ile Val Phe Leu Ala Phe Asp Val
    210                 215                 220 ttt ttc gct gtg ttt tgt gtt gct atg tcc tgt ttc att ggg att gca    720
Phe Phe Ala Val Phe Cys Val Ala Met Ser Cys Phe Ile Gly Ile Ala
225                 230                 235                 240 ctg tgt tgc tgc ttg cct tgt gtc gtt gct att ctg tat gct ctg gct    768
Leu Cys Cys Cys Leu Pro Cys Val Val Ala Ile Leu Tyr Ala Leu Ala
                245                 250                 255 ggc aag gtg ggt gca tca gat gga gat att agt gtc ctt ccg aga tat    816
Gly Lys Val Gly Ala Ser Asp Gly Asp Ile Ser Val Leu Pro Arg Tyr
            260                 265                 270 aga tat tat gat cca agt gag gac agt gag gag gaa acc gat gaa ggt    864
Arg Tyr Tyr Asp Pro Ser Glu Asp Ser Glu Glu Glu Thr Asp Glu Gly
        275                 280                 285 ctg atg atc cct atc ctt aat aac agt gga atg tca acg agt gag cgt    912
Leu Met Ile Pro Ile Leu Asn Asn Ser Gly Met Ser Thr Ser Glu Arg
    290                 295                 300 att ctg ctt cgt gag gat gct gaa tgt tgt gtc tgt ctc tca tca tac    960
Ile Leu Leu Arg Glu Asp Ala Glu Cys Cys Val Cys Leu Ser Ser Tyr
305                 310                 315                 320 gaa gat gga gct gag tta tct gct ctc cct tgc aga cat cac ttc cac   1008
Glu Asp Gly Ala Glu Leu Ser Ala Leu Pro Cys Arg His His Phe His
                325                 330                 335 tgg agt tgt att acc aca tgg ctg cgc atg aac gcg act tgt cca ctc   1056
Trp Ser Cys Ile Thr Thr Trp Leu Arg Met Asn Ala Thr Cys Pro Leu
            340                 345                 350 tgc aag tat aac att ctc gaa atc agt gac agt gca tga               1095
Cys Lys Tyr Asn Ile Leu Glu Ile Ser Asp Ser Ala
        355                 360

<210> SEQ ID NO 2
<211> LENGTH: 364
<212> TYPE: PRT
<213> ORGANISM: Zea mays

<400> SEQUENCE: 2

Met Glu Thr Ala Thr Thr Ser Pro Glu His Pro Leu Leu Arg Arg Ser
1               5                   10                  15

Ser Pro Ser Ser Asn Thr Asn Ala Asp Ala Asp Ser Val Asn Leu Ser
            20                  25                  30

Ser Pro Pro Pro Ser Ala Ala Arg Pro Ser Arg Leu Ala Ala Leu Ile
        35                  40                  45

Gly Arg Val Gly Trp Pro Arg Gly Pro Ser Met Met Val His Glu Ala
    50                  55                  60

Thr Thr Leu Gln Leu His Arg Arg Arg Ala Asp Trp Ala His Ser Arg
```

```
                65                  70                  75                  80
Pro Val Val Thr Leu Asp Ile Ala Trp Asn Val Ala Cys Ala Ala Ala
                        85                  90                  95
Ala Ala Leu Val Leu Ala Ser Ser Ala Lys Asp Ser Pro Val Lys Pro
                100                 105                 110
Leu Arg Leu Trp Leu Val Gly Tyr Ala Ala Gln Cys Leu Val His Val
                115                 120                 125
Gly Ile Val Phe Thr Arg Ser Arg Gly Thr Arg His Ala Trp Gly
130                 135                 140
Pro Ala Ser Asp Val Glu Ser Ala Gly Ala Gly Thr Asp Ser Gly
145                 150                 155                 160
Thr Asp Ser Glu Asp Asp Glu Thr Ala Glu Gly Arg Ser Ser His Ala
                165                 170                 175
Ser Arg Cys Glu Thr Ile Asn Arg Leu Ile Ser Phe Leu Trp Trp Ile
                180                 185                 190
Ile Gly Phe Tyr Trp Leu Val Ser Gly Gly Glu Val Leu Glu Tyr Gly
                195                 200                 205
Ala Pro Arg Leu Tyr Trp Leu Thr Ile Val Phe Leu Ala Phe Asp Val
210                 215                 220
Phe Phe Ala Val Phe Cys Val Ala Met Ser Cys Phe Ile Gly Ile Ala
225                 230                 235                 240
Leu Cys Cys Cys Leu Pro Cys Val Val Ala Ile Leu Tyr Ala Leu Ala
                245                 250                 255
Gly Lys Val Gly Ala Ser Asp Gly Asp Ile Ser Val Leu Pro Arg Tyr
                260                 265                 270
Arg Tyr Tyr Asp Pro Ser Glu Asp Ser Glu Glu Thr Asp Glu Gly
                275                 280                 285
Leu Met Ile Pro Ile Leu Asn Asn Ser Gly Met Ser Thr Ser Glu Arg
                290                 295                 300
Ile Leu Leu Arg Glu Asp Ala Glu Cys Cys Val Cys Leu Ser Ser Tyr
305                 310                 315                 320
Glu Asp Gly Ala Glu Leu Ser Ala Leu Pro Cys Arg His His Phe His
                325                 330                 335
Trp Ser Cys Ile Thr Thr Trp Leu Arg Met Asn Ala Thr Cys Pro Leu
                340                 345                 350
Cys Lys Tyr Asn Ile Leu Glu Ile Ser Asp Ser Ala
                355                 360

<210> SEQ ID NO 3
<211> LENGTH: 1095
<212> TYPE: DNA
<213> ORGANISM: Artificial Sequence
<220> FEATURE:
<223> OTHER INFORMATION: Plant-optimized ZmRING coding region

<400> SEQUENCE: 3
atggagactg ccaccacttc accagagcac cccctcttga ggcgctccag ccccagctcc      60
aacaccaatg ctgatgctga ctctgtcaac ctcagctccc acctcccctc tgctgcaagg     120
ccaagccgtt tggctgcatt gattggaagg gtggggtggc cagaggtcc atccatgatg      180 gttcatgagg ccaccactct ccagctccac agacgcagag cagactgggc acactccaga     240
cctgttgtca cacttgacat agcctggaat gtggcctgtg cagctgcagc tgccttggtt     300
cttgcctcct ctgccaagga ctcacctgtc aaaccactca gactctggtt ggttggctat     360
gctgcccaat gcttggtcca tgtgggcatt gtgttcaccc gttcacgccg tggcacaagg     420
```

```
catgcctggg gacctgcctc tgatgttgaa tctgctggtg ctgggactga cagctctgga      480
actgactctg aggatgacga aacagcagaa gggaggtcca gccatgcaag ccgttgtgag      540
accatcaacc gcttgatctc ctttctctgg tggatcattg gcttctactg gcttgttagc      600
ggtggagagg tccttgagta tggtgcacca aggctttact ggttgaccat tgtgttcctt      660
gcctttgatg tgttctttgc tgtgttctgc gttgccatgt cctgcttcat aggcattgca      720
ctttgctgtt gcttgccttg tgttgtggcc atcctctatg cccttgctgg caaggtgggt      780
gcatcagatg gagacatctc cgtccttccc agatacagat actacgatcc atctgaggac      840
tcagaggaag agacagatga aggtctcatg atcccaatct gaacaattc tgggatgtca      900 acctcagaga ggattctcct tcgtgaggat gctgaatgct gtgtctgctt gtccagctat      960
gaagatggag ctgagttgtc tgctctccct tgcagacatc actttcactg gtcctgcata     1020
accacatggc ttcgcatgaa tgccacttgt cctctctgca agtacaacat tcttgaaatc     1080
tcagactctg cttga                                                      1095
```

<210> SEQ ID NO 4  
<211> LENGTH: 364  
<212> TYPE: PRT  
<213> ORGANISM: Zea mays

<400> SEQUENCE: 4

```
Met Glu Thr Ala Thr Thr Ser Pro Glu His Pro Leu Leu Arg Arg Ser
  1               5                  10                  15

Ser Pro Ser Ser Asn Thr Asn Ala Asp Ala Asp Ser Val Asn Leu Ser
             20                  25                  30

Ser Pro Pro Ser Ala Ala Arg Pro Ser Arg Leu Ala Ala Leu Ile
         35                  40                  45

Gly Arg Val Gly Trp Pro Arg Gly Pro Ser Met Met Val His Glu Ala
     50                  55                  60

Thr Thr Leu Gln Leu His Arg Arg Ala Asp Trp Ala His Ser Arg
 65                  70                  75                  80

Pro Val Val Thr Leu Asp Ile Ala Trp Asn Val Ala Cys Ala Ala Ala
                 85                  90                  95

Ala Ala Leu Val Leu Ala Ser Ser Ala Lys Asp Ser Pro Val Lys Pro
            100                 105                 110

Leu Arg Leu Trp Leu Val Gly Tyr Ala Ala Gln Cys Leu Val His Val
        115                 120                 125

Gly Ile Val Phe Thr Arg Ser Arg Arg Gly Thr Arg His Ala Trp Gly
    130                 135                 140

Pro Ala Ser Asp Val Glu Ser Ala Gly Ala Gly Thr Asp Ser Ser Gly
145                 150                 155                 160

Thr Asp Ser Glu Asp Asp Glu Thr Ala Glu Gly Arg Ser Ser His Ala
                165                 170                 175

Ser Arg Cys Glu Thr Ile Asn Arg Leu Ile Ser Phe Leu Trp Trp Ile
            180                 185                 190

Ile Gly Phe Tyr Trp Leu Val Ser Gly Gly Glu Val Leu Glu Tyr Gly
        195                 200                 205

Ala Pro Arg Leu Tyr Trp Leu Thr Ile Val Phe Leu Ala Phe Asp Val
    210                 215                 220

Phe Phe Ala Val Phe Cys Val Ala Met Ser Cys Phe Ile Gly Ile Ala
225                 230                 235                 240

Leu Cys Cys Cys Leu Pro Cys Val Val Ala Ile Leu Tyr Ala Leu Ala
```

-continued

```
                245                 250                 255
Gly Lys Val Gly Ala Ser Asp Gly Asp Ile Ser Val Leu Pro Arg Tyr
            260                 265                 270

Arg Tyr Tyr Asp Pro Ser Glu Asp Ser Glu Glu Glu Thr Asp Glu Gly
        275                 280                 285

Leu Met Ile Pro Ile Leu Asn Asn Ser Gly Met Ser Thr Ser Glu Arg
    290                 295                 300

Ile Leu Leu Arg Glu Asp Ala Glu Cys Cys Val Cys Leu Ser Ser Tyr
305                 310                 315                 320

Glu Asp Gly Ala Glu Leu Ser Ala Leu Pro Cys Arg His His Phe His
                325                 330                 335

Trp Ser Cys Ile Thr Thr Trp Leu Arg Met Asn Ala Thr Cys Pro Leu
            340                 345                 350

Cys Lys Tyr Asn Ile Leu Glu Ile Ser Asp Ser Ala
        355                 360
```

<210> SEQ ID NO 5
<211> LENGTH: 107
<212> TYPE: PRT
<213> ORGANISM: Zea mays
<220> FEATURE:
<221> NAME/KEY: MISC_FEATURE
<222> LOCATION: (2)..(3)
<223> OTHER INFORMATION: Xaa at positions 2-3 can be any naturally-
      occurring amino acid
<220> FEATURE:
<221> NAME/KEY: MISC_FEATURE
<222> LOCATION: (5)..(43)
<223> OTHER INFORMATION: Xaa at positions 5-43 can be any naturally-
      occurring amino acid, and up to 30 of them may be absent
<220> FEATURE:
<221> NAME/KEY: MISC_FEATURE
<222> LOCATION: (45)..(47)
<223> OTHER INFORMATION: Xaa at positions 45-47 can be any naturally-
      occurring amino acid, and up to 2 of them may be absent
<220> FEATURE:
<221> NAME/KEY: MISC_FEATURE
<222> LOCATION: (49)..(51)
<223> OTHER INFORMATION: Xaa at positions 49-51 can be any naturally-
      occurring amino acid, and up to 1 of them may be absent
<220> FEATURE:
<221> NAME/KEY: MISC_FEATURE
<222> LOCATION: (53)..(54)
<223> OTHER INFORMATION: Xaa at positions 53-54 can be any naturally-
      occurring amino acid
<220> FEATURE:
<221> NAME/KEY: MISC_FEATURE
<222> LOCATION: (56)..(103)
<223> OTHER INFORMATION: Xaa at positions 56-103 can be any naturally-
      occurring amino acid, and up to 44 of them may be absent
<220> FEATURE:
<221> NAME/KEY: MISC_FEATURE
<222> LOCATION: (105)..(106)
<223> OTHER INFORMATION: Xaa at positions 105-106 can be any naturally-
      occurring amino acid

<400> SEQUENCE: 5

```
Cys Xaa Xaa Cys Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Cys Xaa Xaa His
        35                  40                  45

Xaa Xaa Xaa Cys Xaa Xaa Cys Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
```

```
            65                  70                  75                  80
Xaa Xaa Xaa Xaa Xaa Xaa Xaa Xaa Xaa Xaa Xaa Xaa Xaa Xaa Xaa Xaa
                    85                  90                  95

Xaa Xaa Xaa Xaa Xaa Xaa Xaa Cys Xaa Xaa Cys
                100                 105
```